(12) United States Patent
Boronkay

(10) Patent No.: US 11,771,531 B2
(45) Date of Patent: *Oct. 3, 2023

(54) MANDIBULAR ADVANCEMENT AND RETRACTION VIA BONE ANCHORING DEVICES

(71) Applicant: Align Technology, Inc., San Jose, CA (US)

(72) Inventor: Allen R. Boronkay, San Jose, CA (US)

(73) Assignee: ALIGN TECHNOLOGY, INC., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/571,253

(22) Filed: Jan. 7, 2022

(65) Prior Publication Data

US 2022/0233282 A1 Jul. 28, 2022

Related U.S. Application Data

(63) Continuation of application No. 16/424,298, filed on May 28, 2019, now Pat. No. 11,259,901, which is a
(Continued)

(51) Int. Cl.
*A61C 7/08* (2006.01)
*A61C 7/36* (2006.01)
(Continued)

(52) U.S. Cl.
CPC .......... *A61C 8/0096* (2013.01); *A61B 17/663* (2013.01); *A61C 7/08* (2013.01);
(Continued)

(58) Field of Classification Search
CPC .......... A61C 8/0096; A61C 7/08; A61C 7/36; A61C 19/063; A61F 5/56; A61F 5/566; A61F 2005/563; A61F 5/58; A61F 5/0102; A61F 2005/0137; A61F 2005/0139; A61F 2005/0153; A61F 5/026; A61F 5/028; A61F 2210/009; A61F 2250/0067; A61F 2/0022; A61F 2/28; A61F 2/30; A61F 2/36; A61F 2/94; A61F 5/0125; A61F 5/055; A61F 2002/9528; A61F 2250/0004; A61F 2250/0065; A61F 2/013; A61F 2/14; A61F 2/82; A61F 2/95; A61F 5/013;
(Continued)

(56) References Cited

U.S. PATENT DOCUMENTS 5,820,368 A 10/1998 Wolk
6,386,864 B1 5/2002 Kuo
(Continued)

*Primary Examiner* — Tarla R Patel
(74) *Attorney, Agent, or Firm* — FISHERBROYLES, LLP

(57) ABSTRACT

Systems, methods, devices and apparatus for mandibular advancement or retraction via bone anchoring devices are described herein. In various aspects, an apparatus for treating a patient via mandibular advancement or retraction comprises a plurality of anchoring devices positioned in the patient's intraoral cavity. Each of the plurality of anchoring devices can be positioned in bone of the patient's upper jaw or bone of the patient's lower jaw. One or more connecting structures can be removably coupled to and extend between the plurality of anchoring devices in order to displace the lower jaw anteriorly or posteriorly relative to the upper jaw.

20 Claims, 15 Drawing Sheets

Related U.S. Application Data continuation of application No. 14/992,299, filed on Jan. 11, 2016, now Pat. No. 10,517,701.

(60) Provisional application No. 62/161,809, filed on May 14, 2015, provisional application No. 62/103,015, filed on Jan. 13, 2015.

(51) Int. Cl.
*A61C 8/00* (2006.01)
*A61F 5/56* (2006.01)
*A61B 17/60* (2006.01)
*A61B 17/66* (2006.01)

(52) U.S. Cl.
CPC .............. *A61C 7/36* (2013.01); *A61F 5/56* (2013.01); *A61F 5/566* (2013.01); *A61B 2017/603* (2013.01)

(58) Field of Classification Search
CPC .... A61F 9/007; A61F 9/00727; A61B 17/663; A61B 2017/603; A61B 5/4547; A61B 5/4552; A61B 5/4557; A61B 5/682; A61B 5/0534; A63B 71/085; A63B 2071/086; A63B 2017/088; Y10S 602/902; A61N 2/00; A61N 2/002; A61N 2/004; A61N 2/006; A61N 2/008; A61N 1/40; G09B 19/003; G09B 23/28; Y10T 29/49826
See application file for complete search history.

(56) References Cited

U.S. PATENT DOCUMENTS

| | | |
|---|---|---|
| 6,454,565 B2 | 9/2002 | Phan et al. |
| 6,471,511 B1 | 10/2002 | Chishti et al. |
| 6,607,382 B1 | 8/2003 | Kuo et al. |
| 6,783,604 B2 | 8/2004 | Tricca |
| 6,790,035 B2 | 9/2004 | Tricca et al. |
| 6,814,574 B2 | 11/2004 | Abolfathi et al. |
| 6,947,038 B1 | 9/2005 | Anh et al. |
| 7,074,039 B2 | 7/2006 | Kopelman et al. |
| 7,104,792 B2 | 9/2006 | Taub et al. |
| 7,121,825 B2 | 10/2006 | Chishti et al. |
| 7,160,107 B2 | 1/2007 | Kopelman et al. |
| 7,192,273 B2 | 3/2007 | McSurdy, Jr. |
| 7,347,688 B2 | 3/2008 | Kopelman et al. |
| 7,354,270 B2 | 4/2008 | Abolfathi et al. |
| 7,448,514 B2 | 11/2008 | Wen |
| 7,481,121 B1 | 1/2009 | Cao |
| 7,543,511 B2 | 6/2009 | Kimura et al. |
| 7,553,157 B2 | 6/2009 | Abolfathi et al. |
| 7,600,999 B2 | 10/2009 | Knopp |
| 7,658,610 B2 | 2/2010 | Knopp |
| 7,766,658 B2 | 8/2010 | Tricca et al. |
| 7,771,195 B2 | 8/2010 | Knopp et al. |
| 7,854,609 B2 | 12/2010 | Chen et al. |
| 7,871,269 B2 | 1/2011 | Wu et al. |
| 7,878,801 B2 | 2/2011 | Abolfathi et al. |
| 7,878,805 B2 | 2/2011 | Moss et al. |
| 7,883,334 B2 | 2/2011 | Li et al. |
| 7,914,283 B2 | 3/2011 | Kuo |
| 7,947,508 B2 | 5/2011 | Tricca et al. |
| 8,152,518 B2 | 4/2012 | Kuo |
| 8,172,569 B2 | 5/2012 | Matty et al. |
| 8,235,715 B2 | 8/2012 | Kuo |
| 8,292,617 B2 | 10/2012 | Brandt et al. |
| 8,337,199 B2 | 12/2012 | Wen |
| 8,401,686 B2 | 3/2013 | Moss et al. |
| 8,517,726 B2 | 8/2013 | Kakavand et al. |
| 8,562,337 B2 | 10/2013 | Kuo et al. |
| 8,641,414 B2 | 2/2014 | Borovinskih et al. |
| 8,684,729 B2 | 4/2014 | Wen |
| 8,708,697 B2 | 4/2014 | Li et al. |
| 8,758,009 B2 | 6/2014 | Chen et al. |
| 8,771,149 B2 | 7/2014 | Rahman et al. |
| 8,899,976 B2 | 12/2014 | Chen et al. |
| 8,899,977 B2 | 12/2014 | Cao et al. |
| 8,936,463 B2 | 1/2015 | Mason et al. |
| 8,936,464 B2 | 1/2015 | Kopelman |
| 9,022,781 B2 | 5/2015 | Kuo et al. |
| 9,119,691 B2 | 9/2015 | Namiranian et al. |
| 9,161,823 B2 | 10/2015 | Morton et al. |
| 9,241,774 B2 | 1/2016 | Li et al. |
| 9,326,831 B2 | 5/2016 | Cheang |
| 9,433,476 B2 | 9/2016 | Khardekar et al. |
| 9,610,141 B2 | 4/2017 | Kopelman et al. |
| 9,655,691 B2 | 5/2017 | Li et al. |
| 9,675,427 B2 | 6/2017 | Kopelman |
| 9,700,385 B2 | 7/2017 | Webber |
| 9,744,001 B2 | 8/2017 | Choi et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,299,894 B2 | 5/2019 | Tanugula et al. |
| 10,363,116 B2 | 7/2019 | Boronkay |
| 10,383,705 B2 | 8/2019 | Shanjani et al. |
| D865,180 S | 10/2019 | Bauer et al. |
| 10,449,016 B2 | 10/2019 | Kimura et al. |
| 10,463,452 B2 | 11/2019 | Matov et al. |
| 10,470,847 B2 | 11/2019 | Shanjani et al. |
| 10,492,888 B2 | 12/2019 | Chen et al. |
| 10,548,700 B2 | 2/2020 | Fernie |
| 10,555,792 B2 | 2/2020 | Kopelman et al. |
| 10,613,515 B2 | 4/2020 | Cramer et al. |
| 10,639,134 B2 | 5/2020 | Shanjani et al. |
| 10,743,964 B2 | 8/2020 | Wu et al. |
| 10,758,323 B2 | 9/2020 | Kopelman |
| 10,781,274 B2 | 9/2020 | Liska et al. |
| 10,813,720 B2 | 10/2020 | Grove et al. |
| 10,874,483 B2 | 12/2020 | Boronkay |
| 10,881,487 B2 | 1/2021 | Cam et al. |
| 10,912,629 B2 | 2/2021 | Tanugula et al. |
| 10,959,810 B2 | 3/2021 | Li et al. |
| 10,993,783 B2 | 5/2021 | Wu et al. |
| 11,026,768 B2 | 6/2021 | Moss et al. |
| 11,026,831 B2 | 6/2021 | Kuo |
| 11,045,282 B2 | 6/2021 | Kopelman et al. |
| 11,045,283 B2 | 6/2021 | Riley et al. |
| 11,103,330 B2 | 8/2021 | Webber et al. |
| 11,123,156 B2 | 9/2021 | Cam et al. |
| 11,154,382 B2 | 10/2021 | Kopelman et al. |
| 11,166,788 B2 | 11/2021 | Webber |
| 11,174,338 B2 | 11/2021 | Liska et al. |
| 11,219,506 B2 | 1/2022 | Shanjani et al. |
| 11,259,896 B2 | 3/2022 | Matov et al. |
| 11,273,011 B2 | 3/2022 | Shanjani et al. |
| 11,278,375 B2 | 3/2022 | Wang et al. |
| 11,318,667 B2 | 5/2022 | Mojdeh et al. |
| 11,331,166 B2 | 5/2022 | Morton et al. |
| 11,344,385 B2 | 5/2022 | Morton et al. |
| 2002/0192617 A1 | 12/2002 | Phan et al. |
| 2004/0166462 A1 | 8/2004 | Phan et al. |
| 2004/0166463 A1 | 8/2004 | Wen et al. |
| 2005/0014105 A1 | 1/2005 | Abolfathi et al. |
| 2005/0186524 A1 | 8/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | Desimone et al. |
| 2006/0115782 A1 | 6/2006 | Li et al. |
| 2006/0115785 A1 | 6/2006 | Li et al. |
| 2006/0199142 A1 | 9/2006 | Liu et al. |
| 2006/0234179 A1 | 10/2006 | Wen et al. |
| 2008/0118882 A1 | 5/2008 | Su |
| 2008/0160473 A1 | 7/2008 | Li et al. |
| 2008/0286716 A1 | 11/2008 | Sherwood |
| 2008/0286717 A1 | 11/2008 | Sherwood |
| 2009/0280450 A1 | 11/2009 | Kuo |
| 2010/0055635 A1 | 3/2010 | Kakavand |
| 2010/0129763 A1 | 5/2010 | Kuo |
| 2011/0269092 A1 | 11/2011 | Kuo et al. |
| 2014/0067334 A1 | 3/2014 | Kuo |

(56) References Cited

U.S. PATENT DOCUMENTS

| | | |
|---|---|---|
| 2015/0265376 A1 | 9/2015 | Kopelman |
| 2015/0366638 A1 | 12/2015 | Kopelman et al. |
| 2016/0193014 A1 | 7/2016 | Morton et al. |
| 2017/0007359 A1 | 1/2017 | Kopelman et al. |
| 2017/0007360 A1 | 1/2017 | Kopelman et al. |
| 2017/0007361 A1 | 1/2017 | Boronkay et al. |
| 2017/0007366 A1 | 1/2017 | Kopelman et al. |
| 2017/0007386 A1 | 1/2017 | Mason et al. |
| 2017/0135792 A1 | 5/2017 | Webber |
| 2017/0135793 A1 | 5/2017 | Webber et al. |
| 2017/0165032 A1 | 6/2017 | Webber et al. |
| 2018/0360567 A1 | 12/2018 | Xue et al. |
| 2018/0368944 A1 | 12/2018 | Sato et al. |
| 2019/0000592 A1 | 1/2019 | Cam et al. |
| 2019/0000593 A1 | 1/2019 | Cam et al. |
| 2019/0021817 A1 | 1/2019 | Sato et al. |
| 2019/0046297 A1 | 2/2019 | Kopelman et al. |
| 2019/0099129 A1 | 4/2019 | Kopelman et al. |
| 2019/0125494 A1 | 5/2019 | Li et al. |
| 2019/0125497 A1 | 5/2019 | Derakhshan et al. |
| 2019/0152152 A1 | 5/2019 | O'Leary et al. |
| 2019/0175304 A1 | 6/2019 | Morton et al. |
| 2019/0262101 A1 | 8/2019 | Shanjani et al. |
| 2019/0298494 A1 | 10/2019 | Webber et al. |
| 2019/0314119 A1 | 10/2019 | Kopelman et al. |
| 2019/0343606 A1 | 11/2019 | Wu et al. |
| 2020/0000553 A1 | 1/2020 | Makarenkova et al. |
| 2020/0100864 A1 | 4/2020 | Wang et al. |
| 2020/0100865 A1 | 4/2020 | Wang et al. |
| 2020/0100866 A1 | 4/2020 | Medvinskaya et al. |
| 2020/0155276 A1 | 5/2020 | Cam et al. |
| 2020/0188062 A1 | 6/2020 | Kopelman et al. |
| 2020/0214598 A1 | 7/2020 | Li et al. |
| 2020/0214801 A1 | 7/2020 | Wang et al. |
| 2020/0390523 A1 | 12/2020 | Sato et al. |
| 2021/0078357 A1 | 3/2021 | Venkatasanthanam et al. |
| 2021/0147672 A1 | 5/2021 | Cole et al. |

MANDIBULAR ADVANCEMENT AND RETRACTION VIA BONE ANCHORING DEVICES

CROSS-REFERENCE

This application is a continuation of U.S. application Ser. No. 16/424,298, filed May 28, 2019, now U.S. Pat. No. 11,259,901, issued Mar. 1, 2022, which is a continuation of U.S. application Ser. No. 14/992,299, filed Jan. 11, 2016, now U.S. Pat. No. 10,517,701, issued Dec. 31, 2019, which claims the benefit of U.S. Provisional Application No. 62/161,809, filed May 14, 2015, and U.S. Provisional Application No. 62/103,015, filed Jan. 13, 2015, the disclosures of each of which are incorporated herein by reference in their entirety.

BACKGROUND

Obstructive sleep apnea (OSA) is a serious medical condition characterized by complete or partial blockage of the upper airway during sleep. The obstruction may be caused by relaxation of soft tissues and muscles in or around the throat (e.g., the soft palate, back of the tongue, tonsils, uvula, and pharynx) during sleep. OSA episodes may occur multiple times per night, thus disrupting the patient's sleep cycle. Suffers of chronic OSA may experience sleep deprivation, excessive daytime sleepiness, chronic fatigue, headaches, snoring, and hypoxia.

The use of mandibular advancement devices (also referred to as mandibular splints or mandibular advancement splints) has been proposed to treat OSA. A mandibular advancement device is an oral appliance worn in the mouth over the teeth of the upper and/or lower jaws. The device treats sleep apnea by advancing the lower jaw in an anterior direction relative to the upper jaw. This advancement tightens the tissues of the upper airway, thus inhibiting airway obstruction during sleep.

In some instances, however, existing mandibular advancement devices for treating OSA may produce undesirable side effects, such as tooth repositioning, jaw discomfort, and muscle strain. For these reasons, it would be desirable to provide alternative and improved methods and apparatus for treating obstructive sleep apnea and snoring. In particular, it would be desirable to provide alternative and improved methods and apparatus which provide mandibular advancement while reducing or eliminating tooth displacement.

SUMMARY

Systems, methods, devices, and apparatus described herein can be used to treat a patient via mandibular advancement and/or retraction with reduced unintentional tooth repositioning. An apparatus for treating a patient with mandibular advancement and/or retraction may comprise a plurality of anchoring devices for positioning in bone of the patient's intraoral cavity, and one or more connecting structures. The one or more connecting structures can be removably couplable to the anchoring devices so as to displace the lower jaw anteriorly or posteriorly relative to the upper jaw with reduced unintentional tooth repositioning. The anchoring devices can placeable in the bone of the upper jaw, lower jaw, or both jaws. The connecting structures couplable to bone anchoring devices can provide forces to the jaws and with decreased forces to the teeth, in order to reduce unintentional tooth repositioning. The connecting structures and anchoring devices as described herein can produce mandibular advancement and/or retraction while reducing unwanted jaw movements such as vertical displacement of the jaws. The one or more connecting structures can improve control over the patient's jaw configuration during treatment and reduce undesirable side effects such as bruxing of the teeth (teeth clenching or grinding). The apparatus described herein can include at least one connecting structure that provides for the application of anterior and/or posterior forces to the jaws to produce the desired mandibular advancement and/or retraction while inhibiting unwanted jaw movements such as vertical movements (e.g., jaw opening and/or closing movements). For example, the connecting structure can be a stiff or elastic structure capable of supporting bending and/or shear loads in order to apply anterior and/or posterior forces independently from or without applying undesirable vertical forces. The mandibular advancement and/or retraction approaches provided herein can be useful for treating a wide variety of conditions, including but not limited to sleep apnea, snoring, class II malocclusion, and/or class III malocclusion.

In one aspect, an apparatus for treating a patient via mandibular advancement or retraction comprises a plurality of anchoring devices for positioning in the patient's intraoral cavity. Each of the plurality of anchoring devices can be positioned in the bone of the patient's upper jaw or the bone of the patient's lower jaw. One or more connecting structures are provided to be removably coupled to and extend between the plurality of anchoring devices in order to displace the lower jaw anteriorly or posteriorly relative to the upper jaw when in position in the patient's intraoral cavity.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
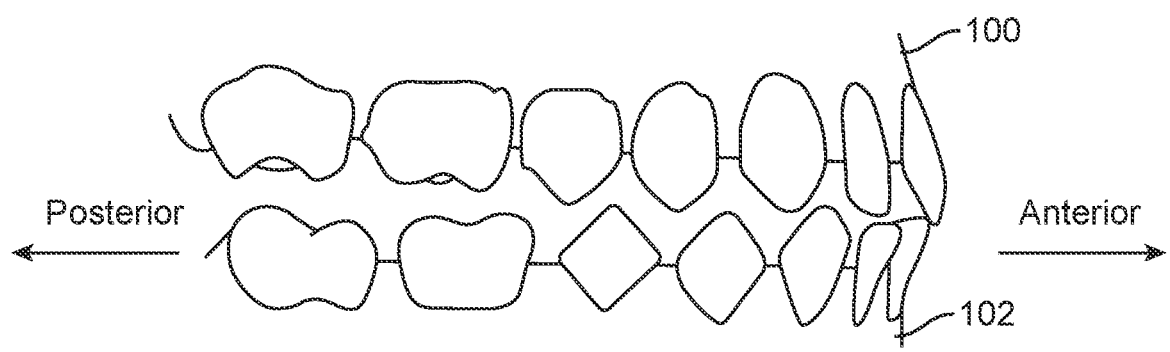
FIG. 1A illustrates a patient's upper and lower jaws in a habitual occlusal position, in accordance with embodiments.

A better understanding of the features and advantages of the present disclosure will be obtained by reference to the following detailed description that sets forth illustrative embodiments, in which the principles of embodiments of the present disclosure are utilized, and the accompanying drawings.

As used herein the terms "torque" and "moment" are treated synonymously.

As used herein the term "and/or" is used as a functional word to indicate that two words or expressions are to be taken together or individually. For example, A and/or B encompasses A alone, B alone, and A and B together.

Systems, methods, devices and apparatus for mandibular advancement and/or retraction via bone attachment are described herein. In various aspects, an apparatus for treating a patient via mandibular advancement or retraction comprises a plurality of anchoring devices for positioning in the patient's intraoral cavity. Each of the plurality of anchoring devices can be positioned in bone of the patient's upper jaw or bone of the patient's lower jaw. One or more connecting structures can be removably coupled to and extend between the plurality of anchoring devices in order to displace the lower jaw anteriorly or posteriorly relative to the upper jaw.

In various aspects, a method for treating a patient via mandibular advancement or retraction comprises positioning a plurality of anchoring devices in the patient's intraoral cavity. Each of the plurality of anchoring devices can be positioned in bone of the patient's upper jaw or bone of the patient's lower jaw. The method can comprise removably coupling one or more connecting structures to the plurality of anchoring devices. The one or more connecting structures can extend between the plurality of anchoring devices in order to displace the lower jaw anteriorly or posteriorly relative to the upper jaw.

In some embodiments, the one or more connecting structures are arranged to displace the lower jaw anteriorly relative to the upper jaw when in position in a patient's intraoral cavity in order to treat sleep apnea in the patient. Alternatively or in combination, other types of jaw displacements can be produced to treat other conditions, e.g., class II or class III malocclusions. If desired, the embodiments herein can also be used to control jaw displacement along other directions, e.g., along a lateral (left-right) direction, a vertical (jaw opening-closing) direction, or combinations thereof.

The one or more connecting structures can extend between the plurality of anchoring devices in order to displace the lower jaw to a target location along an anterior-posterior direction during use. In some embodiments, the one or more connecting structures are arranged to produce an anterior-posterior force component that displaces the lower jaw anteriorly or posteriorly relative to the upper jaw during use. The anterior-posterior force component can be produced by the one or more connecting structures independently of a vertical force component produced by the one or more connecting structures. For example, the one or more connecting structures, when coupled to the plurality of anchoring devices, may be capable of producing an anterior-posterior force component without producing a vertical force component. Optionally, the one or more connecting structures, when coupled to the plurality of anchoring devices, may produce the anterior-posterior force component with a magnitude greater than a magnitude of a vertical force component, or may produce the anterior-posterior force component without producing a vertical force component.

In some embodiments, the one or more connecting structures and the plurality of anchoring devices are arranged to constrain vertical displacement of the lower jaw relative to the upper jaw when in position in a patient's intraoral cavity. For instance, the vertical displacement can be constrained in order to inhibit bruxing and/or inhibit contact between teeth of the lower jaw and teeth of the upper jaw.

Various types of connecting structures can be used in order to produce mandibular advancement and/or retraction without producing unwanted vertical jaw movements, e.g., in order to inhibit bruxing. For example, the one or more connecting structures comprise at least one connecting structure configured to support one or more of a bending load or a shear load to allow application of anterior-posterior force components independently of vertical force components. For example, the one or more connecting structures can comprise at least one stiff structure, at least one elastic structure, or combinations thereof. In some embodiments, the one or more connecting structures comprise at least one elastic structure, and the elastic structure can comprise a spring or an elastic band. Optionally, the at least one elastic structure can comprise a stiffness sufficient to support one or more of a bending load or a shear load.

In some embodiments, the one or more connecting structures comprise at least one stiff structure and the design of the stiff structure can be varied as desired. In some embodiments, the at least one stiff structure comprises a stiffness of at least about 5 N/mm. The at least one stiff structure can comprise a stiffness sufficient to support one or more of a bending load or a shear load. The at least one stiff structure can comprise a stiff plate. The stiff plate can be removably coupled to three or more of the plurality of anchoring devices. The stiff plate can be removably coupled to two or more anchoring devices positioned in the bone of the upper jaw. The stiff plate can be removably coupled to two or more anchoring devices positionable in the bone of the lower jaw.

The one or more connecting structures can be arranged to apply a moment to at least one of the upper jaw or the lower jaw when in position in a patient's intraoral cavity. The moment can result from advancing and/or retracting the mandible without producing unwanted vertical jaw movements. The one or more connecting structures can be arranged to apply the moment to the upper jaw and/or lower jaw when in position in a patient's intraoral cavity. The moment can be applied by a connecting structure configured to support a bending and/or shear load in order to apply the moment. The connecting structure can be coupled to the upper jaw or the lower jaw via at least one anchoring device that constrains rotation of the connecting structure along at least one direction of rotation in order to apply the moment at a location near the at least one anchoring device.

In some embodiments, the one or more connecting structures are configured to perform one or more of the following functions when in position in a patient's intraoral cavity: produce an anterior-posterior force component independently of a vertical force component, produce an anterior-posterior force component without producing a vertical force component, support a bending load and/or a shear load, or apply a moment to the upper jaw and/or lower jaw.

Any number and combination of anchoring devices can be used in accordance with embodiments herein. For instance, the plurality of anchoring devices can comprise three or more anchoring devices. The anchoring devices can be coupled to the connecting structures using various mechanisms. In some embodiments, the one or more connecting structures are removably couplable to the plurality of anchoring devices by, for example, snap-fit couplings, magnetic couplings, interference fits, locking surfaces, adhesives, removable fasteners, cam locks, interlocking mechanical couplings, fastening features, or combinations thereof. The one or more connecting structures can be removably coupled to the plurality of anchoring devices such that the one or more connecting structures can be coupled to and removed from the plurality of anchoring devices by the patient. In some embodiments, the one or more connecting structures are removably couplable to the plurality of anchoring devices such that the one or more connecting structures can be coupled to and removed from the plurality of anchoring devices by the patient without using tools. Alternatively, the one or more connecting structures can be removably coupled to the plurality of anchoring devices such that the one or more connecting structures can be coupled to and removed from the plurality of anchoring devices by the patient using a tool (e.g., a simple tool customized for use with the connecting structures).

In some embodiments, a connecting structure can be coupled to an anchoring device and another appliance or device located in the patient's intraoral cavity. For example, the one or more connecting structures can include at least one connecting structure removably coupled to at least one anchoring device and a shell appliance which can be positioned on the upper jaw or the lower jaw. The one or more connecting structures can include at least one connecting structure removably coupled to at least one anchoring device and an attachment positionable on at least one tooth of the upper jaw or the lower jaw. The plurality of anchoring devices can include at least one dental implant (e.g., a dental prosthesis implanted in bone of the jaw such as a crown or bridge) positionable in the upper jaw or the lower jaw of the patient and the one or more connecting structures comprise at least one connecting structure removably couplable to the at least one dental implant.

In some embodiments, the one or more connecting structures comprise at least one connecting structure having a shape customized to the patient's oral geometry.

In various aspects, an apparatus for treating a patient via mandibular advancement and retraction comprises a plurality of anchoring devices positionable in the patient's intraoral cavity. Each of the plurality of anchoring devices can be positioned in bone of the patient's upper jaw or bone of the patient's lower jaw. A first one or more connecting structures can be removably couplable to and extendable between a first subset of the plurality of anchoring devices during a first treatment phase in order to displace the lower jaw anteriorly relative to the upper jaw during the first treatment phase. A second one or more connecting structures can be removably couplable to and extendable between a second subset of the plurality of anchoring devices during a second treatment phase so as to displace the lower jaw posteriorly relative to the upper jaw during the second treatment phase. Optionally, the first and/or second one or more connecting structures can be used in combination with an orthodontic appliance (e.g., a tooth repositioning aligner).

In various aspects, a method for treating a patient via mandibular advancement and retraction comprises positioning a plurality of anchoring devices in the patient's intraoral cavity. Each of the plurality of anchoring devices can be positioned in bone of the patient's upper jaw or bone of the patient's lower jaw. The method can comprise removably coupling a first one or more connecting structures to a first subset of the plurality of anchoring devices, wherein the first one or more connecting structures extend between the first subset of the plurality of anchoring devices in order to displace the lower jaw anteriorly relative to the upper jaw during a first treatment phase. The method can comprise removably coupling a second one or more connecting structures to a second subset of the plurality of anchoring devices, wherein the second one or more connecting structures extend between the second subset of the plurality of anchoring devices in order to displace the lower jaw posteriorly relative to the upper jaw during a second treatment phase.

The embodiments provided herein can be used in various types of orthodontic treatments. For example, the first treatment phase can include treatment for sleep apnea of the patient and the second treatment phase comprises treatment for a malocclusion of the patient. The malocclusion can include a class III malocclusion. The first treatment phase can be performed when the patient is asleep and the second treatment phase can be performed when the patient is awake.

In some embodiments, the first one or more connecting structures differ from the second one or more connecting structures. The first subset of the plurality of anchoring devices can differ from the second subset of the plurality of anchoring devices.

In some embodiments, the first one or more connecting structures are arranged to produce an anterior force component that displaces the lower jaw anteriorly relative to the upper jaw, and the second one or more connecting structures are arranged to produce a posterior force component that displaces the lower jaw posteriorly relative to the upper jaw. The anterior force component can be produced by the first one or more connecting structures independently of a vertical force component produced by the first one or more connecting structures, and the posterior force component can be produced by the second one or more connecting structures independently of a vertical force component produced by the second one or more connecting structures. At least one of the first one or more connecting structures or the second one or more connecting structures can be configured to constrain vertical displacement of the lower jaw relative to the upper jaw. In some embodiments, at least one of the first one or more connecting structures or the second one or more connecting structures is configured to support one or more a bending load or a shear load. For instance, at least one of the first one or more connecting structures or the second one or more connecting structures can comprise at least one stiff structure. In some embodiments, at least one of the first one or more connecting structures or the second one or more connecting structures is arranged to apply a moment to at least one of the upper jaw or the lower jaw In various aspects, methods are provided herein for providing any of the apparatus described herein.

In some aspects, systems, methods, devices and apparatus described herein include methods for treating sleep apnea in a patient, said methods including placing an oral appliance in the patient's mouth, wherein the appliance removably attaches at one location to one or more bone anchors in the patient's upper jaw and wherein the appliance removably attaches at another location to the patient's lower jaw, wherein the appliance imparts a force between the upper jaw and the lower jaw which advances the lower jaw to inhibit apnea in the patient. The appliance can be used to position the mandible and support any forces and/or moments needed to produce the desired positioning. In some aspects, the patient inserts and removes the appliance from the patient's mouth. The appliance can include elastic elements, stiff elements, and/or combinations thereof. In some aspects, the appliance removably attaches to two or more bone anchors in the patient's upper jaw and/or in the patient's lower jaw. The bone anchors and the attachment location on the appliance can be configured to self-center when the appliance is secured to the anchors.

Although some embodiments herein are described in the context of mandibular advancement, it shall be appreciated that the systems, methods, devices, and apparatus of the present disclosure are equally applicable to producing and/or controlling other types of jaw movements, such as mandibular retraction, lateral jaw movements, vertical jaw movements, etc. Additionally, although some embodiments herein are presented in the context of sleep apnea treatment, this is not intended to be limiting, and it shall be understood that the systems, methods, devices, and apparatus of the present disclosure can be applied to treat any condition where mandibular advancement and/or retraction is beneficial, such as class II or class III malocclusions, TMJ dysfunction, and so on.

Turning now to the drawings, in which like numbers designate like elements in the various figures, FIG. 1A illustrates an upper jaw 100 and a lower jaw 102 of a patient in a habitual occlusal position, in accordance with embodiments. The habitual occlusal position can correspond to the normally closed position of the upper and lower jaws 100, 102. Patients suffering from sleep apnea may experience restricted airflow due to blockage of the upper airway if the upper and lower jaws 100, 102 remain in their habitual occlusal relationship during sleep due to relaxation of soft tissue in or around the upper airway.

Figure 1B:
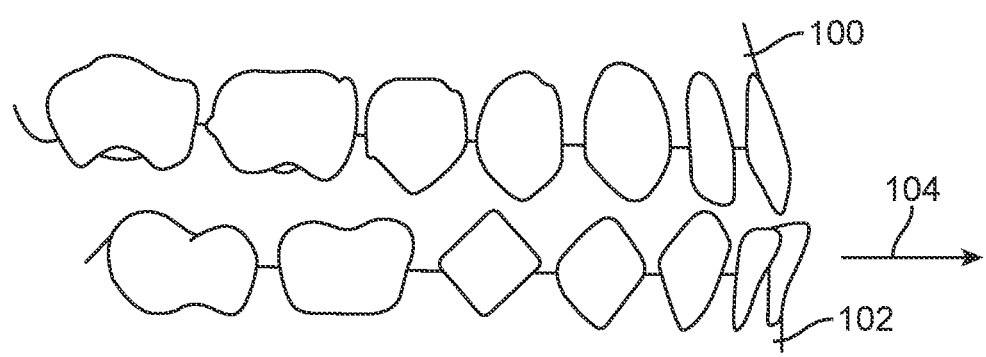
FIG. 1B illustrates a patient's upper and lower jaws in a "mandible-advanced" occlusal position, in accordance with use of embodiments.

FIG. 1B illustrates the upper jaw 100 and lower jaw 102 in a "mandible-advanced" occlusal position, in accordance with use of embodiments. In the advanced position, the lower jaw 102 has been displaced from its habitual position along an anterior direction (indicated by arrow 104) such that the lower jaw 102 is now positioned anteriorly relative to the upper jaw 100. The advanced position of the lower jaw 102 can be used to tighten the soft tissues of the upper airway, thus maintaining unobstructed airflow during sleep.

In some embodiments, apparatus and methods are provided for mandibular advancement where forces which protrude the mandible (lower jaw) are arranged to be applied directly to the upper and/or lower jaw bones, rather than indirectly via the teeth. Usually no or reduced forces will be applied to the teeth in order to reduce or eliminate unintended tooth repositioning or displacement, such as inclination of anterior teeth. Prior to sleep, the patient can removably install an oral apparatus to effect mandibular advancement, also referred to herein as a mandibular advancement appliance or device. In some embodiments, the oral apparatus is anchored to both the upper jaw bone (the maxilla) and to the lower jaw bone (the mandible) and is configured to provide a fixed or adjustable displacement of the lower jaw bone relative to the upper jaw bone. For example, the apparatus can apply an anterior force to the lower jaw bone in order to displace the lower jaw anteriorly relative to the upper jaw.

The displacement position may be fixed, e.g., being provided by a relatively stiff or rigid connecting structure such as a plate or other fixture which maintains a fixed displacement between the upper and lower jaws. In other embodiments, the displacement position may be variable, e.g., resulting from a relatively compliant or flexible connecting structure such as spring or other elastic attachment been the upper and lower jaws. In still other embodiments, the displacement may be continuously or variably adjustable. Such adjustable apparatus may employ motors or other adjustment mechanisms as described in co-pending U.S. application Ser. No. 14/992,175, filed Jan. 11, 2016, titled "SYSTEMS AND METHODS FOR POSITIONING A PATIENT'S MANDIBLE IN RESPONSE TO SLEEP APNEA STATUS," the full disclosure of which is incorporated herein by reference.

In some embodiments, the apparatus provided herein are couplable to permanent or temporary anchoring devices positionable in or on one or more anatomical structures of the patient's intraoral cavity, such as the patient's upper and/or lower jaw bones. As used herein "anchor" and "anchoring device" are used interchangeably. By coupling the apparatus to anchoring devices placed in bone, mandibular advancement and/or retraction forces can be applied directly to the patient's jaws and not to the teeth, thus reducing the incidence of unwanted tooth repositioning (e.g., caused by long-term application of advancement and/or retraction forces on the teeth). Anchoring devices can include hardware suitable for fixation into bone, such as bone fasteners, screws, plates, rods, and connectors. The anchoring devices can be made of metal, glass, composite, plastic, or any other suitable material, and/or combinations thereof. In some embodiments, an anchoring device can include a screw for securing the anchoring device to a patient's upper and/or lower jaw bones. Optionally, the anchoring device can be a dental implant for use in the patient's intraoral cavity, e.g., a screw for supporting a crown, bridge, or other prosthesis. In some embodiments, one or more holes suitable for securing an anchoring device such as a screw can be drilled into the upper and/or lower jaws and used to secure one or more anchoring devices.

In performing the methods of the present invention, bone anchoring devices which may be similar to conventional orthodontic TADs (temporary anchoring devices) can placed at preselected locations in the bones of the patient's upper and lower jaws. The anchors may be temporary but will often be permanent. Temporary anchors may be similar to TADs of a type commonly used in orthodontic procedures. In some embodiments, since existing TADs are intended to be temporary and sleep apnea generally requires long-term treatment, the anchoring devices are likely to need somewhat different features to allow for long-term use, e.g., as for implants or hip or knee replacement components. If the anchoring devices are intended to be for long-term use and/or are permanent, they may be configured to encourage bone ingrowth, for example, with appropriate porosity or surface treatments. Permanent anchors can be similar to the post anchors which are used for tooth replacement, for example.

An apparatus for mandibular advancement can include any suitable number of anchoring devices, such as one, two, three, four, five, six, seven, eight, nine, ten, or more anchoring devices. The anchoring devices can be positioned in the patient's upper jaw bone only, lower jaw bone only, or in both the upper and lower jaw bones. The number of anchoring devices positioned in a patient's intraoral cavity can be optimized according to a desired treatment plan. In some embodiments, one, two, three, four, five, six, seven, eight, nine, ten, or more anchoring devices are present in the intraoral cavity. Optionally, anchoring devices can be distributed evenly between the left and right sides of the intraoral cavity, such that an even number of anchoring devices is used. The placement of anchoring devices in the left and right sides of the intraoral cavity may or may not be symmetric In some embodiments, one, two, three, four, five, or more anchoring devices are positioned in the bone of the upper jaw. In some embodiments, one, two, three, four, five, or more anchoring devices are positioned in the bone of the lower jaw. For example, in some embodiments, two anchoring devices are positioned in the bone of the upper jaw, and two anchoring devices are positioned in bone of the lower jaw. In some embodiments, one anchoring device is positioned in the bone of the upper jaw, and one anchoring device is positioned in bone of the lower jaw. In some embodiments, one anchoring device is positioned in the bone of the upper jaw, and two anchoring devices are positioned in bone of the lower jaw. In some embodiments, two anchoring devices are positioned in the bone of the upper jaw, and one anchoring device are positioned in bone of the lower jaw. In some embodiments, more than two anchoring devices are positioned in either or both of the lower jaw and the upper jaw. In some embodiments, one or more anchoring devices positioned in the upper jaw are anterior to one or more anchoring devices positioned in the lower jaw. In some embodiments, one or more anchoring devices positioned in the upper jaw are posterior to one or more anchoring devices positioned in the lower jaw.

The couplings between the apparatus and the one or more anchoring devices in the patient's upper and/or lower jaw bones can be removable or non-removable couplings. As used herein, unless otherwise noted, "coupled" can mean either directly coupled or indirectly coupled (e.g., via one or more intermediate structures such as adapters). As used herein, unless otherwise noted, "coupled" can mean either removably coupled or non-removably coupled. As used herein, unless otherwise noted, "removably coupled" and "releasably coupled" are interchangeable and mean that the coupled structures or elements can be coupled and decoupled readily by an end-user (e.g., a patient). In some embodiments, a removably coupled structure can be coupled and decoupled by the user without aid of a treating professional and/or tools. In other embodiments, a removably coupled structure can be coupled and decoupled by the user with aid of a simple tool (e.g., a hex key), which may or may not be customized for use with the removable coupling. Examples of removable couplings include but are not limited to snap-fit couplings, magnetic couplings, interference fits, locking surfaces, adhesives, removable fasteners (e.g., hook and loop fasteners such as VELCRO-type fasteners, touch fasteners, thumb screws, nuts, bolts, pins, rivets), cam locks, interlocking mechanical couplings (e.g., mechanical coupling elements that can be decoupled only when in a certain configuration), fastening features (e.g., hooks, loops, bands, posts), and the like. In contrast, a non-removably coupled structure may be permanently affixed and incapable of separation without being damaged, or may not be capable of being coupled or decoupled by the user without aid of a professional and/or tools.

In some embodiments, the apparatus includes one or more connecting structures that can be removably or non-removably coupled to the one or more anchoring devices and extend between the one or more connecting structures in order to displace the lower jaw relative to the upper jaw to produce mandibular advancement and/or retraction when in position in a patient's intraoral cavity. Any suitable number and combination of connecting structures can be used. For example, an apparatus can include one, two, three, four, five, or more connecting structures to be positioned in the patient's intraoral cavity. Examples of connecting structures include but are not limited to bands, rods, plates, springs, strips, 3D printed structures, structures with curved, organic, and/or custom-fitted shapes, or combinations thereof. The connecting structures can include structures made of metal, glass, composite, plastic, natural or synthetic rubber, or any other suitable material, and/or combinations thereof. Connecting structures can be coupled to anchoring devices using any suitable coupling mechanism known in the art. For example, as discussed above and herein, connecting structures can be coupled to anchoring devices by snap-fit couplings, magnetic couplings, interference fits, locking surfaces, adhesives, removable fasteners, cam locks, interlocking mechanical couplings, fastening features, and the like.

The connecting structures can be coupled to any suitable number of anchoring devices in order to produce mandibular advancement and/or retraction forces when in position in a patient's intraoral cavity. The number of anchoring devices positioned in a patient's intraoral cavity and the number of anchoring devices to which one or more connecting structures are coupled can both vary according to the plan of treatment and can both be optimized, e.g., so as to eliminate or minimize an obstruction of the airway and/or prevent sleep apnea and/or snoring. The number of anchoring devices positioned in a patient's intraoral cavity, and the number of anchoring devices to which one or more connecting structures are coupled, can be optimized so as to apply forces to the upper and/or lower jaws that cause a desired or planned displacement of the lower jaw relative to the upper jaw. In some embodiments, a connecting structure is removably coupled to one, two, three, four, five, six, seven, eight, nine, ten or more anchoring devices. A connecting structure can be coupled to anchoring devices in the upper jaw only, the lower jaw only, or both jaws. In some embodiments, a connecting structure is removably coupled to one, two, three, four, five or more anchoring devices positioned in the bone of the upper jaw. In some embodiments, a connecting structure is removably coupled to one, two, three, four, five or more anchoring devices positioned in the bone of the lower jaw.

Figure 2:
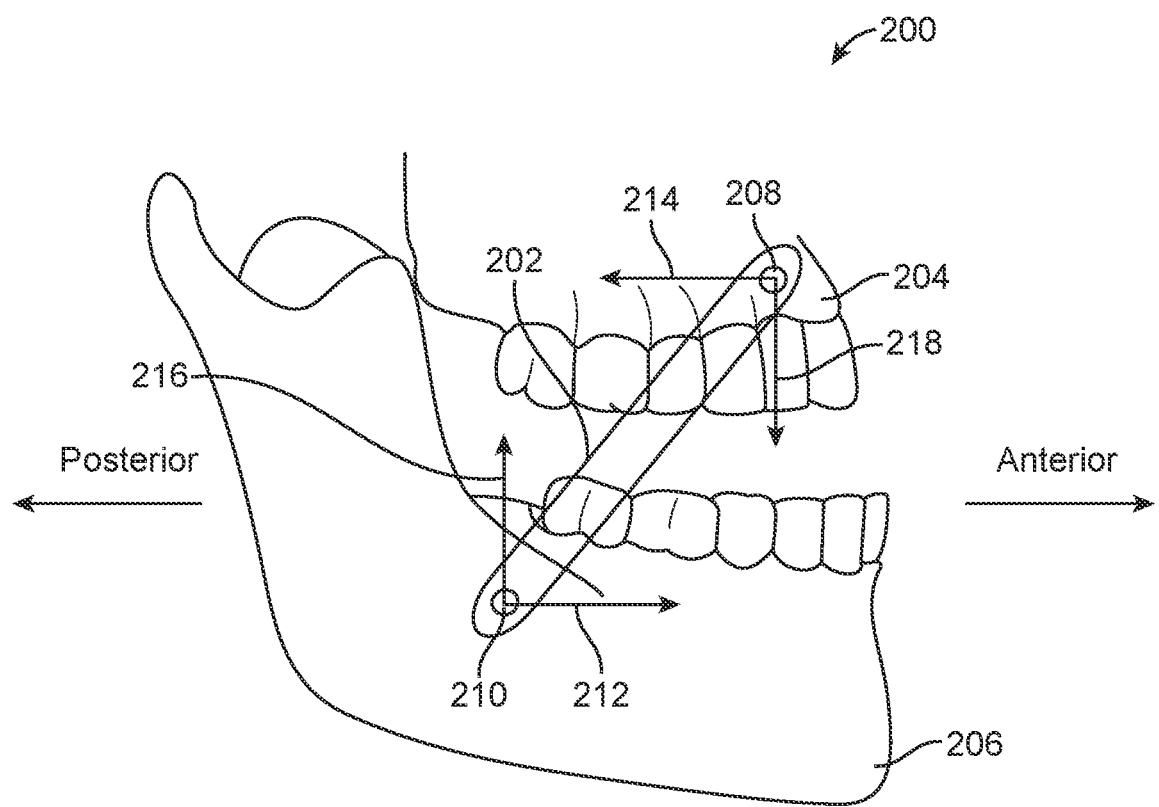
FIG. 2 illustrates a first exemplary oral apparatus which comprises an elastic tension element attachable at an upper end to an anchor on the upper jaw and oriented to elastically draw the lower jaw forward when in position in a patient's intraoral cavity, in accordance with embodiments.

FIG. 2 illustrates an oral apparatus 200 having an elastic connecting structure 202, in accordance with embodiments. In FIG. 2, the oral apparatus 200 comprises an elastic connecting structure 202 (depicted herein as an elastic band) to apply forces to the upper and lower jaws 204, 206 to open the airway by pulling the lower jaw 206 forward relative to the upper jaw 204. When in position in a patient's intraoral cavity, the elastic structure 202 can be removably coupled to the upper and lower jaws 204, 206 via an upper anchoring device 208 in the upper jaw 204 and a lower anchoring device 210 in the lower jaw 206. The upper anchoring device 208 can be positioned anteriorly relative to the lower anchoring device 210 such that the tension in the elastic structure 202 applies a tensile force including an anterior force component 212 to advance the lower jaw 206. Similarly, an equal and opposite posterior force component 214 can be applied to the upper jaw 204 by the tensile force in the elastic structure 202. Because the forces are primarily applied directly to the bones rather than to the teeth, unintentional tooth movement that can be caused by existing dental apparatus used to correct sleep apnea is avoided.

In some embodiments, the tension in the elastic structure 202 also applies vertical force components 216, 218 to the patient's jaws 204, 206 when in position in a patient's intraoral cavity. "Vertical" or "occlusal" may be used herein to refer to the direction of jaw movement during jaw opening and/or closing. In some aspects, an occlusal or vertical force and/or displacement of the lower jaw relative to the upper jaw may be undesirable. The application of such vertical forces can cause undesirable vertical displacement of the patient's jaws, e.g., jaw opening or jaw closing movements, that may lead to undesirable side effects such as muscle strain, teeth grinding or clenching, and TMJ pain. As used herein, "vertical displacement" may refer to displacement of the jaws away from a habitual vertical position, e.g., a natural resting position of the jaws during sleep. The habitual vertical position may be a mouth open position, mouth closed position, or any intermediate position, depending on the particular patient. For example, in the embodiment of FIG. 2, the vertical force components 216, 218 produced by the tension in the elastic connecting structure 202 may cause the jaws 204, 206 to be pulled together, which may result in undesirable occlusal contact forces and/or bruxing.

In order to avoid such unintentional side effects, various embodiments herein provide connecting structures coupled to anchoring devices so as to apply a force system and/or one or more moments when in position in a patient's intraoral cavity to produce a desired anterior and/or posterior displacement of the lower jaw relative to the upper jaw while minimizing, eliminating, or otherwise constraining unwanted displacements of the lower jaw relative to the upper jaw. The unwanted displacements can be, e.g., unwanted vertical displacements that produce jaw opening or jaw closing movements as described herein. For example, the connecting structure(s) can be configured to allow and/or restrict movement of the lower jaw relative to the upper jaw in any of three translational and in any of three rotational dimensions. In some embodiments, the connecting structure creates anterior-posterior (horizontal) movements and/or rotational movements while constraining vertical movements. In some embodiments, the connecting structure(s) can be arranged extending between the plurality of anchoring devices in order to displace the lower jaw to a target location along an anterior-posterior direction.

In some embodiments of the methods, devices, systems and apparatus described herein, an anterior and/or posterior displacement of the lower jaw relative to the upper jaw produced by the force system and/or one or more moments during use is greater than a vertical displacement of the lower jaw relative to the upper jaw produced by the force system. In some embodiments, the force system and/or one or more moments produce substantially no vertical displacement of the lower jaw relative to the upper jaw during use. In some embodiments, an anterior and/or posterior displacement of the lower jaw relative to the upper jaw produced by the force system and/or one or more moments is greater than a vertical displacement of the lower jaw relative to the upper jaw produced by the force system and the moment. In some embodiments, the force system and/or one or more moments produce substantially no vertical displacement of the lower jaw relative to the upper jaw.

Connecting structures and anchoring devices described herein can be arranged to displace the lower jaw anteriorly with an amount of anterior-posterior force in an anterior-posterior direction greater than amounts of force in vertical directions. The connecting structures and anchoring devices can be arranged to inhibit force to the lower jaw in vertical directions. The connecting structures and anchoring devices can be arranged to limit movement of the lower jaw in vertical directions when the lower jaw has advanced anteriorly or posteriorly. The connecting structures and anchoring devices can be arranged to displace the lower jaw anteriorly or posteriorly with substantially no vertical displacement of the lower jaw relative to the upper jaw. The connecting structures and anchoring devices can be arranged to displace the lower jaw anteriorly or posteriorly with an amount of anterior or posterior displacement greater than an amount of vertical displacement of the lower jaw relative to the upper jaw. The connecting structures and anchoring devices can be arranged to urge the lower jaw anteriorly or posteriorly with an amount of anterior or posterior displacement greater than a vertical amount of displacement of the lower jaw relative to the upper jaw, the vertical displacement comprising no more than about 5%, 10%, 15%, 20%, 25%, 30%, 35%, 40%, 45%, 50%, 60%, 70%, 80%, 90% or 100% of the anterior or posterior displacement. Optionally, the connecting structures and anchoring devices can be arranged to permit vertical movements of the jaws within a certain range while simultaneously advancing or retracting the mandible, as described further herein.

Unwanted displacements such as vertical displacements can be constrained or eliminated by a variety of ways while still permitting anterior-posterior jaw displacement during use. In some embodiments, the connecting structures are arranged to produce one or more anterior-posterior force components independently of vertical force components in order to inhibit undesirable vertical displacement during mandibular advancement and/or retraction. Certain types of connecting structures may not be capable of producing anterior-posterior force components independently of and/or without producing any vertical force components, which may result in unwanted vertical jaw movements when anterior-posterior forces are applied. For instance, structures that are not capable of supporting bending and/or shear loads (e.g., due to insufficient stiffness within the sagittal plane) such as elastic bands may not be capable of producing an anterior-posterior force component without also applying vertical force components to the jaws. Stiffness within the sagittal plane may refer to stiffness with respect to all three degrees of freedom of movement within the sagittal plane (e.g., two degrees of translation and one degree of rotation). Referring again to FIG. 2, in some embodiments, the elastic connecting structure 202 is not capable of supporting bending and/or shear loads and relies solely on tensile force to pull the lower jaw 206 forward, such that anterior-posterior force components 212, 214 cannot be produced without also generating vertical force components 216, 218. A similar result may be produced by a connecting structure that is not capable of supporting bending and/or shear loads and relies solely on compressive force to push the lower jaw forward.

Accordingly, the characteristics of the connecting structures and/or anchoring devices herein can be selected to permit production and application of anterior-posterior force components independently of vertical force components in use. Such connecting structures, when coupled to anchoring devices, may be capable of producing an anterior-posterior force component without producing a vertical force component. In some embodiments, the one or more connecting structures, when coupled to the plurality of anchoring devices, produce an anterior-posterior force component having a magnitude greater than a magnitude of a vertical force component, or produce an anterior-posterior force component without producing any vertical force component.

Various types of connecting structures can be used to enable production of anterior-posterior force components independently of any vertical force components. For example, in some embodiments, the connecting structure can be a structure capable of supporting bending and/or shear loads, e.g., acts like a beam within the sagittal plane by having sufficient stiffness to resist bending and/or shear. The bending and/or shear load can be produced, for example, by reaction forces applied by the jaws on the connecting structure in response to the mandibular advancement produced by the connecting structure. In some embodiments, such connecting structures can be stiff structures that resist deformation when a bending and/or shear load is applied. In other embodiments, a connecting structure that supports a bending and/or shear load can have some amount of compliance and can exhibit some amount of deformation when a bending and/or shear load is applied. The extent to which the connecting structure deforms under a bending and/or shear load can be adjusted to achieve a desired degree of control over the resultant jaw configuration. Alternatively or in combination, multiple connecting structures transmitting loads to multiple anchoring devices can be used in order to form an assembly capable of supporting bending and/or shear loads. For example, the connecting structures can be arranged in a truss-like assembly (e.g., the opposing ends of each connecting structure are coupled to different anchoring devices such that each connecting structure acts as a two-force member) capable of supporting bending and/or shear loads.

The properties of the connecting structures described herein can be varied as desired, e.g., with respect to size (e.g., length, width, thickness), shape, material properties (e.g., stiffness, elasticity), and so on. For instance, in some embodiments, a connecting structure can be an elastic structure that deforms when placed under a load (e.g., forces and/or moments). Examples of elastic structures include but are not limited to bands, plates, strips, springs, spring-loaded devices, and the like. The apparatus herein can include at least one elastic connecting structure, such as one, two, three, four, five, or more elastic connecting structures. The stiffness of the elastic structure (e.g., stiffness within the sagittal plane) can be varied as desired. In some embodiments, the elastic structure has a stiffness less than or equal to about 0.1 N/mm. In some embodiments, the elastic structure has a stiffness less than or equal to about 1 N/mm. In some embodiments, the elastic structure has a stiffness less than or equal to about 5 N/mm. Through the use of appropriate materials and geometry, the stiffness can be tailored to achieve desired motion constraints for different loadings or motions, such as different stiffnesses in the anterior and/or posterior direction versus the vertical direction. Designs can include variations in which the connecting structure is elastic for some loadings or motions and stiff for others. In some embodiments, the elastic connecting structure is capable of supporting a bending and/or shear load, e.g., has sufficient stiffness within the sagittal plane.

As another example, in some embodiments, the apparatus herein include at least one stiff connecting structure, such as one, two, three, four, five, or more stiff connecting structures. In some embodiments, a stiff connecting structure can be a stiff or rigid structure that is resistant to deformation caused by applied loads (e.g., bending and/or shear loads), such as a stiff plate or plate-like structure, rod, or bar. A stiff connecting structure may maintain its shape with minimal or no distortion when forces and/or moments are applied, e.g., by the patient's jaws. A stiff connecting structure can be used to support bending and/or shear loads. In some embodiments, stiff connecting structures that are stiffer than the elastic structures presented herein can be used to transmit force from the upper jaw to the lower jaw. With proper design, these stiff structures can be used in compression rather than tension if desired. This can give the doctor more flexibility in placing the anchoring device, which can allow the doctor to avoid anatomically difficult placements and to have better control in directing the resulting forces to create the desired jaw position.

A stiff structure can have a stiffness that is greater than that of the elastic structures described herein. In some embodiments, the stiff structure has a stiffness of at least about 5 N/mm. In some embodiments, the stiff structure has a stiffness of at least about 20 N/mm. In some embodiments, the stiff structure has a stiffness of at least about 100 N/m. Accordingly, a stiff connecting structure can be used to maintain the upper and lower jaws in a fixed position relative to each other and reduce unwanted displacements (e.g., vertical displacements) as described herein. The use of stiff connecting structures can improve the degree of control over the resultant position of the jaws. Through the use of appropriate materials and/or geometry, the stiffness can be tailored to achieve desired motion constraints for different loadings or motions, such as different stiffnesses in the anterior and/or posterior direction versus the vertical direction. Designs can include variations in which the connecting structure is stiff for some loadings or motions and elastic for others.

In some embodiments, a connecting structure that produces anterior and/or posterior displacement of the lower jaw while inhibiting undesirable vertical displacements will apply one or moments to the upper jaw, the lower jaw, or both when in position in a patient's intraoral cavity. A moment may be produced, for example, when the connecting structure applies anterior-posterior force components to the jaws without applying vertical force components, thus resulting in a force couple. In some embodiments, a connecting structure capable of supporting bending and/or shear loads is also capable of supporting and applying a moment. A connecting structure capable of supporting and applying a moment can be a stiff structure that exhibits substantially no deformation under load, such as the embodiments described herein. In other embodiments, a connecting structure used for applying moments to the jaw(s) can be an elastic structure that exhibits some degree of compliance (e.g., experiences some deformation under loading), but still has sufficient stiffness to support the moment load. For example, a connecting structure for applying a moment load can have a rotational stiffness of about 5 N-mm/radian, or from about 0.1 N-mm/radian to about 100 N-mm/radian. A connecting structure that has some compliance can reduce patient discomfort, e.g., by permitting relatively small translational and/or rotational movements while maintaining the advanced position of the lower jaw.

The shape of a connecting structure (stiff or elastic) can be varied as desired. For example, the structure can be a rod, bar, plate, or plate-like structure. The plate or plate-like structure can be substantially flat or planar. The plate or plate-like structure can have a circular, elliptical, triangular, rectangular, or other polygonal shape, and/or combinations and/or variants thereof, such as shapes having both corners and rounded edges. Optionally, the connecting structure can have a shape customized to conform the patient's oral geometry. In such embodiments, the connecting structure can have a curved, organic, and/or irregular shape.

The number and position of anchoring devices to which the connecting structures are removably coupled can be varied as desired. For example, the number of anchoring devices on the upper and lower jaws can be configured to anteriorly displace the lower jaw relative to the upper jaw in use. The number of anchoring devices on the upper and lower jaws can also be configured to restrict vertical movement of the lower jaw relative to the upper jaw. To achieve a desired or planned displacement of the lower jaw relative to the upper jaw, the connecting structure can be removably coupled to one or more anchoring devices positioned as desired on the upper jaw and one or more anchoring devices positioned as desired on the lower jaw. In some cases, it may be desirable for the connecting structure to be couplable to one anchoring device on the lower jaw and more than one anchoring device on the upper jaw. In other cases, it may be desirable for the connecting structure to be couplable to one anchoring device on the upper jaw and more than one anchoring device on the lower jaw. In still other cases, it may be desirable for the connecting structure to be couplable to more than one anchoring device on both the upper jaw and the lower jaw.

Figure 3A:
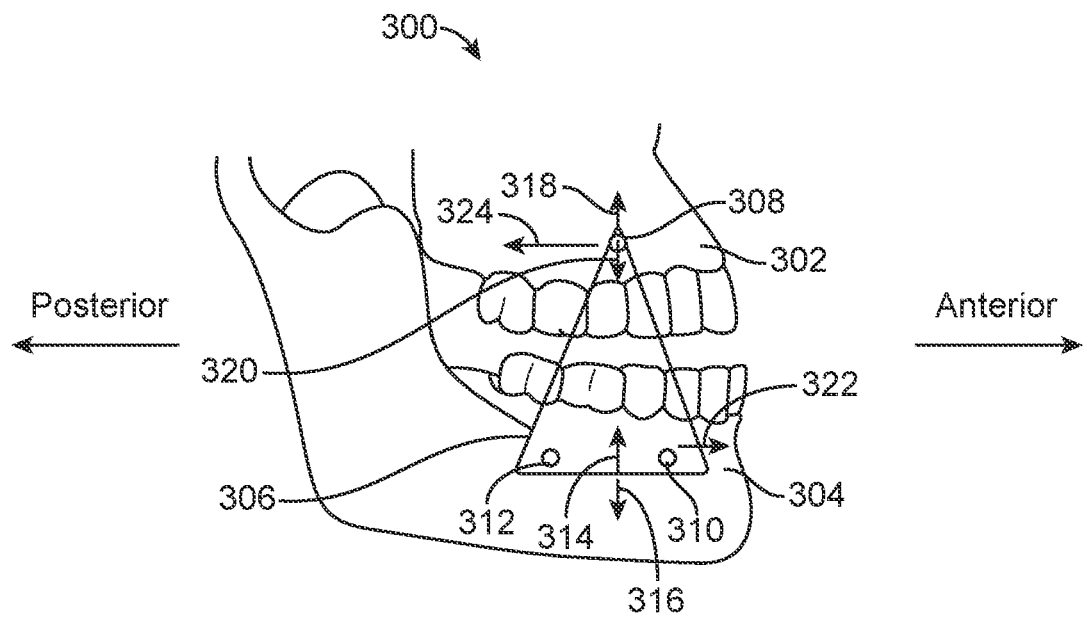
FIGS. 3A and 3B illustrates a pair of fixed plate embodiments attachable to the upper and lower jaws, optionally through bone anchors located at two or more attachment points, in accordance with embodiments.
Figure 3B:
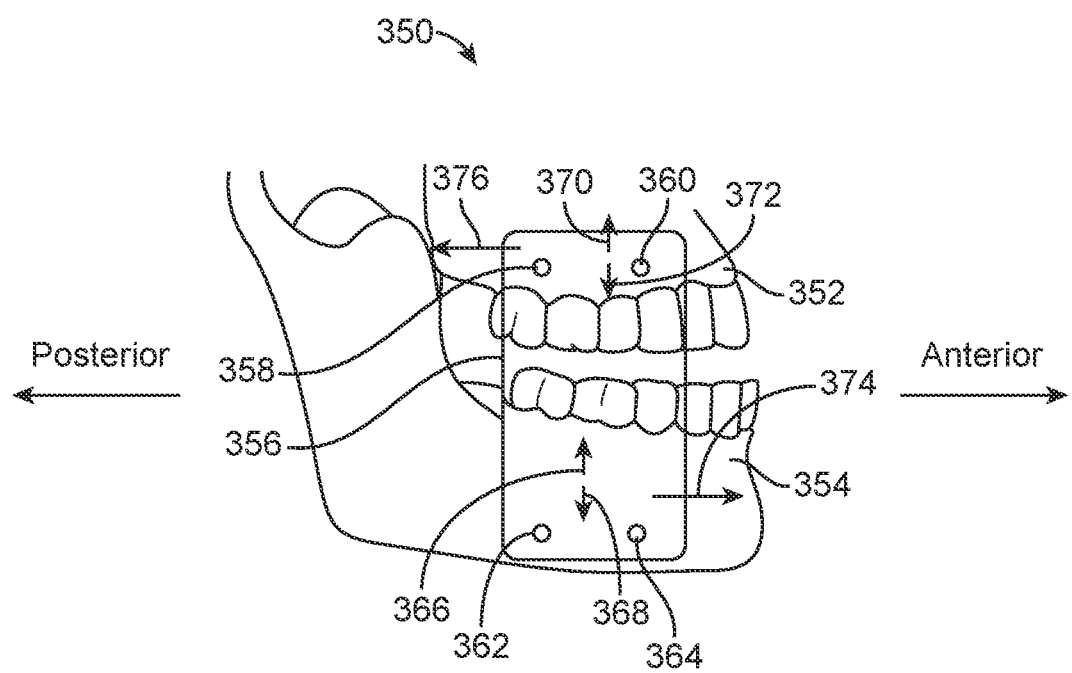

FIGS. 3A and 3B illustrate apparatus with connecting structures capable of applying anterior-posterior force components independently of any vertical force components when in position in a patient's intraoral cavity, in accordance with embodiments. By using plates which optionally are securable to two or more anchors in either or both jaws, both the relative advancement and degree of opening of the jaws can be controlled. In FIG. 3A, apparatus 300 comprises a triangular plate-like connecting structure 306 that is coupled to anchoring device 308 positioned on upper (maxillary) jaw 302 and coupled to anchoring devices 310 and 312 positioned on lower jaw 304. The connecting structure 306 can have sufficient stiffness within the sagittal plane to be capable of supporting bending and/or shear loads. Anchoring devices 308, 310 and 312 can be positioned such that the connecting structure 306 applies an anterior force 322 on lower jaw 304 that causes anterior displacement of the lower jaw relative to the upper jaw. A corresponding posterior force 324 can be applied on the upper jaw 302 by the connecting structure 306. Forces 322, 324 form a force couple resulting in a moment being applied to the jaws. In order to be in equilibrium, the jaws may apply a counteracting moment (not shown) to the connecting structure 306. The anterior-posterior forces 322, 324 can be applied by the connecting structure 306 to the jaws independently of any vertical force components, such that there is no tendency of the jaws to be pulled together or pushed apart when the apparatus 300 is worn.

Optionally, in some embodiments, the geometry (e.g., height) of the connecting structure 306 can be selected to bias the jaws in a desired vertical configuration when in position in a patient's intraoral cavity, e.g., a partially open configuration that inhibits bruxing. Movement of the jaws away from the configuration defined by the connecting structure geometry may result in generation of vertical forces on the jaws as the connecting structure 306 restricts the movement of the jaws. For example, the upper jaw 302 may apply a downward vertical force 320 to connecting structure 306 through anchoring device 308 and lower jaw 304 may apply an upward vertical force 314 to connecting structure 306 through anchoring devices 310 and 312, e.g., when the patient attempts to close their jaws. In this embodiment, vertical displacement of the lower jaw relative to the upper jaw can be restricted because connecting structure 306 is sufficiently stiff to resist the loads from the upper and lower jaws and is securely coupled to anchoring devices 308, 310 and 312 (e.g., does not translate and/or rotate relative to the anchoring devices 308, 310, 312). Accordingly, connecting structure 306 can apply an upward vertical force 318 to upper jaw 302 through anchoring device 308 that is equal and opposite to downward vertical force 320, and can apply a downward vertical force 316 to lower jaw 304 through anchoring devices 310 and 312 that is equal and opposite to upward vertical force 314, thereby reducing or inhibiting movement of the lower jaw relative to the upper jaw. Similarly, the connecting structure 306 can also resist opening movements of the jaws (e.g., upward vertical forces applied by the upper jaw and/or downward vertical forces applied by the lower jaw). Alternatively or in combination, the connecting structure 306 can exhibit some degree of compliance such that small vertical movements are permitted even as the jaws are biased into the specified configuration, e.g., to improve patient comfort.

In FIG. 3B, apparatus 350 comprises rectangular plate-like connecting structure 356 that, when in position in a patient's intraoral cavity, is coupled to anchoring devices 358 and 360 positioned on upper (maxillary) jaw 352 and coupled to anchoring devices 362 and 364 positioned on lower jaw 354. The connecting structure 356 can have sufficient stiffness within the sagittal plane to be capable of supporting bending and/or shear loads. Anchoring devices 358, 360, 362 and 364 can be positioned so as to apply an anterior force 374 that causes anterior displacement of the lower jaw relative to the upper jaw. A corresponding posterior force 376 can be applied on the upper jaw 352 by the connecting structure 356. Forces 374, 376 form a force couple resulting in a moment being applied to the jaws, and the jaws may apply a counteracting moment (not shown) to the connecting structure 356. Similar to the embodiment of FIG. 3A, the anterior-posterior forces 374, 376 can be applied by the connecting structure 356 to the jaws independently of any vertical force components, such that there is no tendency of the jaws to be pulled together or pushed apart when the apparatus 350 is worn.

Similar to the embodiment of FIG. 3A, the geometry of the connecting structure 356 can be selected to restrict the jaws to a desired vertical configuration. Vertical displacement of the lower jaw relative to the upper jaw can be restricted because connecting structure 356 is sufficiently stiff and is sufficiently coupled to anchoring devices 358, 360, 362 and 364. In some embodiments, if the patient attempts to move the jaws away from the configuration specified by the connecting structure 356, upper jaw 352 may apply a downward vertical force 372 to connecting structure 356 through anchoring devices 358 and 360, and lower jaw 354 may apply an upward vertical force 366 to connecting structure 356 through anchoring devices 362 and 364. Connecting structure 356 can apply an upward vertical force 370 to upper jaw 352 through anchoring devices 358 and 360 that is equal and opposite to downward vertical force 372, and can apply a downward vertical force 368 to lower jaw 354 through anchoring devices 362 and 364 that is equal and opposite to upward vertical force 366, thereby reducing or inhibiting movement of the lower jaw relative to the upper jaw. Similarly, jaw opening movements can also be reduced or inhibited by the connecting structure 356. Optionally, the connecting structure 356 can exhibit some degree of compliance such that small vertical movements are permitted even as the jaws are biased into the specified configuration, e.g., to improve patient comfort.

Figure 4A:
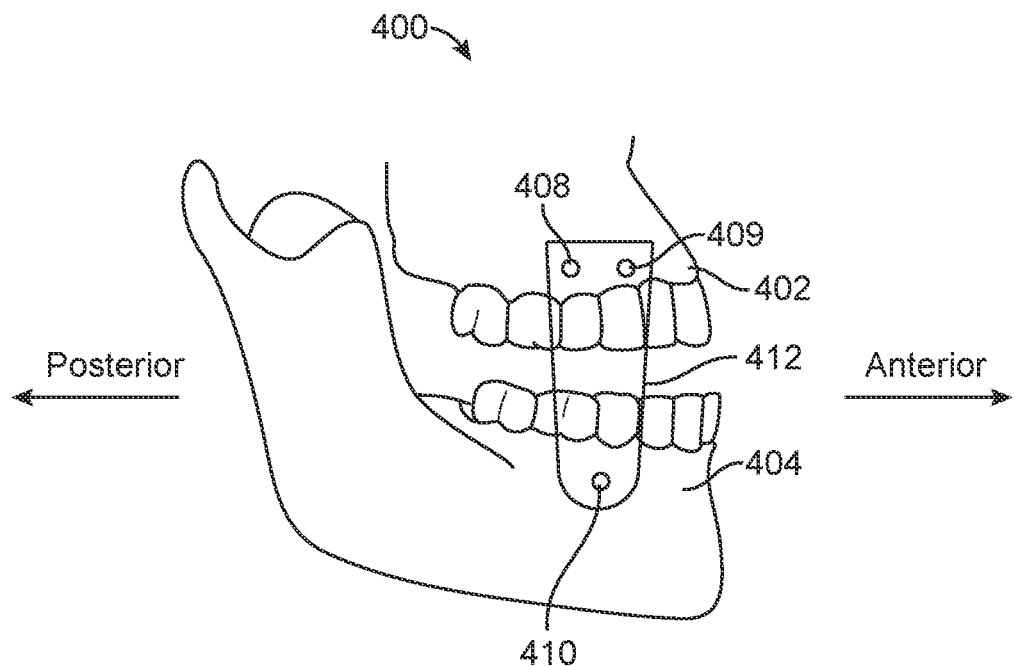
FIG. 4A illustrates an oral apparatus having a rigid or compliant connecting structure that can support bending and/or shear loads, in accordance with embodiments.
Figure 4B:
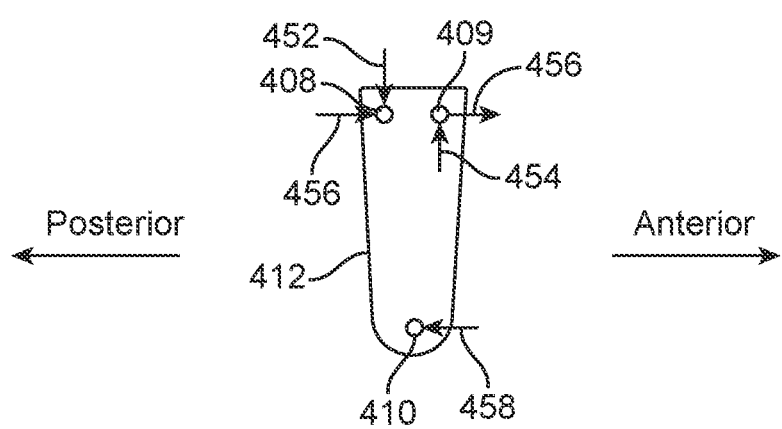
FIG. 4B illustrates reaction force vectors from the maxilla and mandible acting on the structure of FIG. 4A, in accordance with embodiments.

FIGS. 4A and 4B illustrate an apparatus with a connecting structure capable of applying anterior-posterior force components independently of any vertical force components when in position in a patient's intraoral cavity, in accordance with embodiments. In the embodiment shown in FIG. 4A, the apparatus 400 comprises a triangular-shaped plate-like connecting structure 412 that can support bending and/or shear loads. Connecting structure 412 can be removably coupled to anchoring devices 408 and 409 that are positioned in bone of the patient's upper jaw 402 and can be removably coupled to anchoring device 410 that is positioned in bone of the patient's lower jaw 404. Similar to other embodiments presented herein, the connecting structure 412 and anchoring devices 408, 409, 410 can be arranged to apply a force system to advance and/or retract the lower jaw 404 relative to the upper jaw 402.

FIG. 4B illustrates the reaction forces exerted on the plate member of FIG. 4A by the upper and lower jaws 402, 404 during advancement. The reaction forces can be applied on the connecting structure 412 by the upper and lower jaws 402, 404 when the lower jaw 404 is anteriorly displaced relative to the upper jaw 402 as a result of the force system applied by the apparatus 400. In the embodiment shown in FIG. 4B, horizontal reaction forces 456 are applied in an anterior direction to connecting structure 412 by the upper jaw 402 through anchoring devices 408 and 409, and horizontal reaction force 458 is applied in a posterior direction to connecting structure 412 by the lower jaw 404 through anchoring device 410, thus resulting in a clockwise rotational reaction force being applied to connecting structure 412. Downward vertical reaction force 452 is applied to connecting structure 412 by the upper jaw through anchoring device 408, and upward vertical reaction force 454 is applied to connecting structure 412 by the upper jaw through anchoring device 409, resulting in a counterclockwise rotational reaction force being applied to connecting structure 412 near the anchoring devices 408, 409. Connecting structure 412 can have sufficient stiffness to support bending and/or shear loads such as reaction forces 452, 454, 456 and 458.

Various types of anchoring devices can be used in combination with the connecting structures described herein in order to allow the apparatus to apply moments to the jaws and/or support bending and/or shear loads. In some embodiments, the anchoring device can allow and/or constrain certain movements of the connecting structure relative to the anchoring device (e.g., with respect to up to three degrees of freedom in translation and up to three degrees of freedom in rotation) when the connecting structure is coupled to the anchoring device. Constraint of translational and/or rotation movements can allow the connecting structure to support bending and/or shear loads at or near the coupled anchoring device(s). Optionally, an anchoring device can permit certain movements while inhibiting other movements. For example, a rotatable anchoring device (e.g., a pivot, ball joint, pin, etc.) can permit some or all rotational movements of a coupled connecting structure relative to the anchoring device while constraining some or all translational movements of the connecting structure. In some embodiments, a freely rotatable anchoring device (e.g., a pivot, ball joint) permits rotational movement of the connecting structure about to the anchoring device with respect to three degrees of freedom in rotation. A freely rotatable anchoring device may constrain some or all translational movement of the connecting structure relative to the anchoring device. As another example, a partially rotatable anchoring device can constrain some rotational movements of a coupled connecting structure. In some embodiments, a pin anchoring device permits rotation of the connecting structure about the axis of the pin only and constrains rotational movements in other directions. A partially rotatable anchoring device may constrain some or all translational movement of the connecting structure relative to the anchoring device. For instance, a pin anchoring device may or may not permit translation of connecting structure along the pin axis. In yet another example, a non-rotatable anchoring device can constrain all rotational movements of a coupled connecting structure. A non-rotatable anchoring device may constrain some or all translational movement of the connecting structure relative to the anchoring device.

In some embodiments, rotational constraint of a connecting structure by an anchoring device (e.g., with respect to one, two, or three degrees of rotational freedom) can enable the connecting structure to support and/or transmit moment loads to the jaw at or near the location of the anchoring device. For instance, a connecting structure can apply a moment at or near the location of a partially rotatable or non-rotatable anchoring device. A connecting structure can be coupled to any suitable number and combination of anchoring device types (e.g., only pin anchoring devices, only pivot anchoring devices, a combination of pin and pivot anchoring devices, etc.) in order to produce moments on the jaws at one or more specified locations.

For instance, referring again to FIG. 4A, the anchoring devices 408, 409, and 410 can be pivot anchoring devices. The pivot anchoring devices can be two-dimensional pivots that permit rotation of the connecting structure 412 within the vertical plane, thus allowing the mandible 404 to rotate relative to the maxilla 402. Optionally, the pivot anchoring devices can be three-dimensional pivots that also permit rotation of the connecting structure 412 within the transverse plane. The use of three-dimensional pivots can permit at least some side-to-side motions of the mandible (e.g., along the transverse direction) even as the apparatus forces the mandible to advance anteriorly, to improve patient comfort.

Figure 5A:
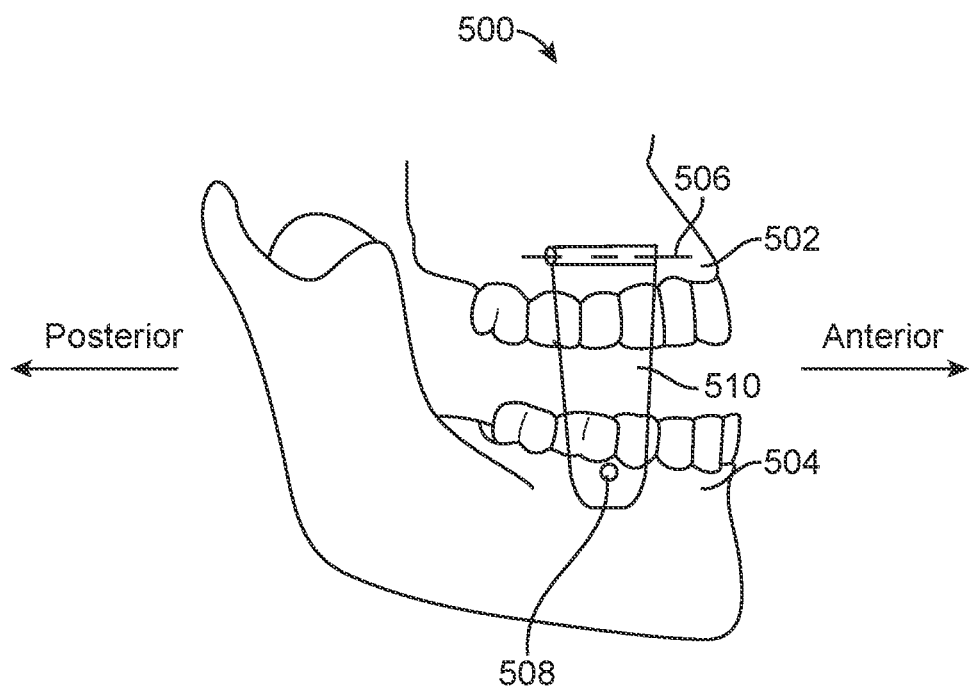
FIG. 5A illustrates an oral apparatus having a connecting structure couplable to the jaws via a pin anchoring device and pivot anchoring device, in accordance with embodiments.

In the embodiment shown in FIG. 5A, apparatus 500 comprises connecting structure 510 which when in position in a patient's intraoral cavity are coupled to pin anchoring device 506 positioned on maxillary jaw bone 502 and pivot anchoring device 508 positioned on mandibular jaw bone 504. In other embodiments, the pin anchoring device 506 can be positioned on the mandible 504 and the pivot anchoring device 508 can be positioned on the maxilla 502. Pin anchoring device 506 can be a partially rotatable anchoring device that permits rotation of connecting structure 510 about the longitudinal pin axis only and restricts all other rotational movements of connecting structure 510. Optionally, pin anchoring device 506 can also constrain horizontal (anterior-posterior) sliding movements of connecting structure 510 along the horizontal (anterior-posterior) axis of pin anchoring device 506. In contrast, pivot anchoring device 508 can restrict translational sliding movements of connecting structure 510 while allowing rotational movements of connecting structure 510 about a pivoting axis centered about pivot anchoring device 508. Accordingly, the apparatus 500 can permit some rotation of the mandible 504 relative to the maxilla 502, which can increase patient comfort. Additionally, due to the rotational constraint placed on the connecting structure 510 by the pin anchoring device 506, the connecting structure 510 can apply a moment to the maxilla 502 near the pin anchoring device 506.

Figure 5B:
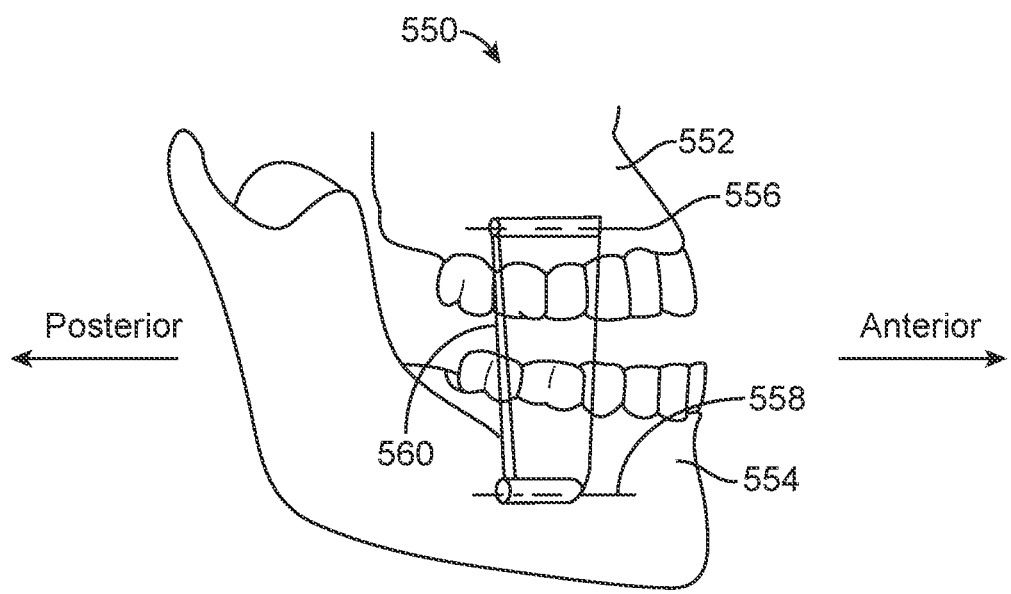
FIG. 5B illustrates an oral apparatus having a connecting structure couplable to the jaws via two pivot anchoring devices, in accordance with embodiments.

In the embodiment shown in FIG. 5B, apparatus 550 comprises connecting structure 560 which when in position in a patient's intraoral cavity is coupled to pin anchoring device 556 positioned on maxillary jaw bone 552 and is coupled to pin anchoring device 558 positioned on mandibular jaw bone 554. Pin anchoring devices 556 and 558 can restrict rotational movements of connecting structure 560 while allowing for substantially horizontal (anterior-posterior) sliding movements of connecting structure 560 along the horizontal (anterior-posterior) axes of pin anchoring devices 556 and 558. The apparatus 550 can restrict the rotation of the mandible 554 relative to the maxilla 552. The rotational constraints of the connecting structure 560 at pin anchoring devices 556, 558 can allow the connecting structure 560 to apply moments to the maxilla 556 and mandible 554 near pin anchoring devices 556, 558 respectively.

Figure 6:
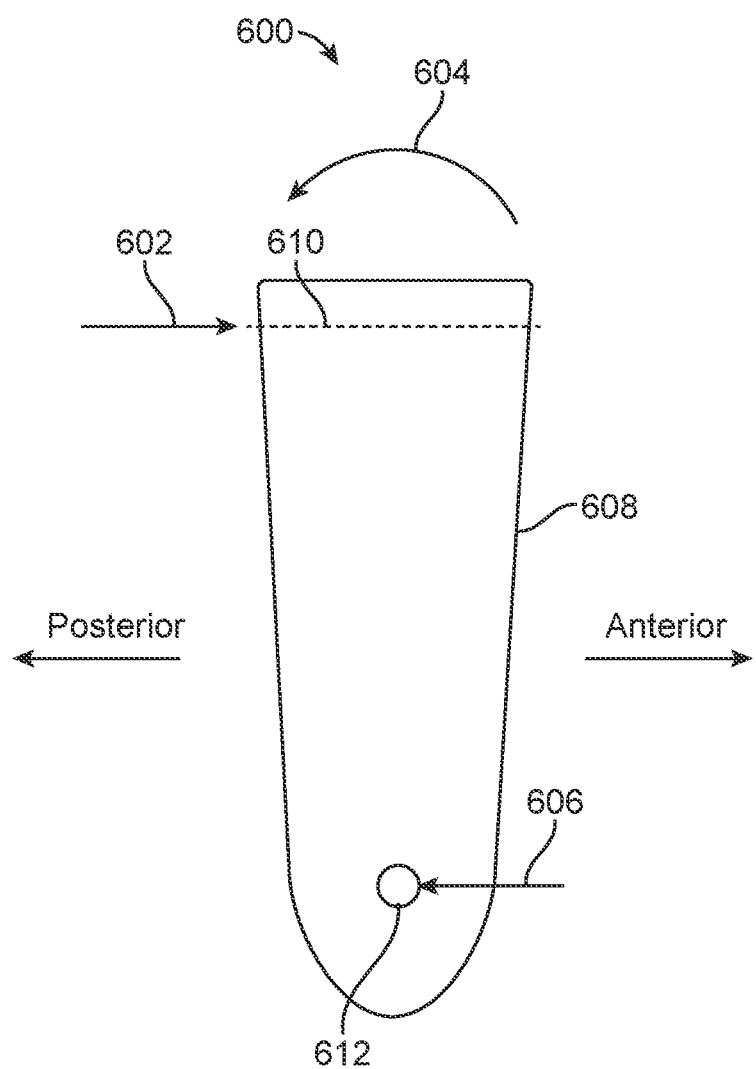
FIG. 6 illustrates reaction force vectors from the maxilla and mandible acting on a connecting structure that can support moment loads when in position in a patient's intraoral cavity, in accordance with embodiments.

FIG. 6 is a free body diagram 600 depicting forces applied to a connecting structure 608, in accordance with embodiments. Similar to the embodiment of FIG. 5A, connecting structure 608 is coupled to the maxilla when in position in a patient's intraoral cavity via a pin anchoring device 610 and the mandible via a pivot anchoring device 612, respectively. The connecting structure 608 and anchoring devices 610, 612 can be arranged such that the connecting structure 608 displaces the mandible in the anterior direction in use, resulting in the mandible applying a posterior reaction force 606 on the connecting structure 608 at anchoring device 612, the maxilla applying an anterior reaction force 602 on the connecting structure 608 at anchoring device 610, and the maxilla applying a counterclockwise moment 604 on the connecting structure 608 at anchoring device 610.

The different types of connecting structures described herein can be combined in various ways to produce a force system for mandibular advancement while limiting unwanted jaw displacements. In some embodiments, for instance, the connecting structures can include a combination of elastic and stiff structures described herein in order to apply a desired force system, e.g., to permit certain jaw movements while restricting others. The connecting structures can include stiff structures combined with flexing or compliant structures such as elastics or other springs or spring-like features that allow the flexing structures to be mounted at locations such as particular target locations on the patient's jaw. Specific anchoring locations can be selected to align the forces generated as desired, e.g., to pull and/or push the mandible forward without also creating jaw opening or closing forces. The oral apparatus may alternatively comprise stiff structures or only slightly compliant structures to lock the relationship of the mandible and maxilla in place. Stiff and compliant regions may also be built into the same apparatus attached to the anchoring devices so that a single part (or optionally a left-right pair of parts) can provide the advantages described above with a simple, low cost device. In order to anchor stiff or compliant parts that need to carry moment loads, multiple anchoring devices may be used and/or the anchor devices may be built so that each can constrain multiple degrees of freedom. The present disclosure includes embodiments optionally using connecting structures (e.g., plates) which may have both relatively stiff (more rigid) portions and relatively elastic (less rigid) portions in a single structure or assembly to create the desired mechanical behavior, for example by appropriate design of the part geometry, through the use of a plurality of materials, or both.

Figure 7:
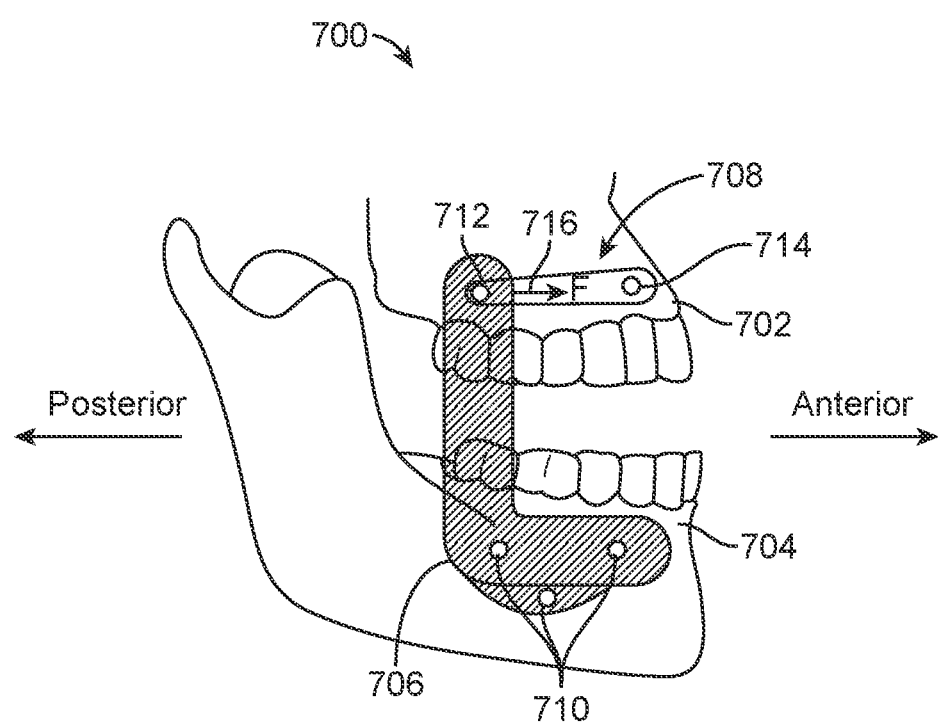
FIG. 7 illustrates a combination elastic/fixed plate oral apparatus, in accordance with embodiments.

FIG. 7 shows apparatus 700 having a combination of relatively stiff and relative elastic connecting structures, in accordance with embodiments. Stiff connecting structure 706 can be an L-shaped plate that is removably couplable to three anchoring devices 710 positioned on lower jaw 704 that fully support stiff connecting structure 706. Stiff connecting structure 706 can also be removably coupled to elastic connecting structure 708 at coupling portion 712 of the stiff connecting structure 706. Elastic connecting structure 708 can be removably coupled to anchoring device 714 positioned on upper jaw 702 such that the tension in elastic connecting structure 708 applies anterior force (F) 716 to stiff connecting structure 706 at coupling portion 712. Accordingly, stiff connecting structure 708 applies posterior force to lower jaw 704 via point anchors 710. In some embodiments, the elastic connecting structure 708 and stiff connecting structure 706 are discrete components and are arranged and configured to draw or pull the mandible forward in an anterior direction in use without also creating vertical opening or closing forces of the jaws, or clenching of the teeth. For example, if the force 716 exerted by elastic connecting structure 708 is substantially aligned with the center of rotation of the TMJ, the forces on the upper and lower jaws 702, 704 will not substantially rotate the lower jaw 704 open or closed. In alternative embodiments, the elastic connecting structure 708 and stiff connecting structure 706 can be arranged to produce jaw opening and/or closing movements if desired.

Anchoring devices of the present disclosure can have features to control the position and/or orientation of one or more connecting structures, and/or to provide for adequate coupling to the connecting structures. In some embodiments, anchoring devices have features configured to withstand applied forces and/or moments without substantially deforming or decoupling from one or more connecting structures. Anchoring devices described herein can comprise features such as pins, screws (including but not limited to thumbscrews), snap-fit couplings, magnetic couplings, nuts, bolts, rivets, interference fits, locking surfaces, adhesives, removable fasteners (e.g., hook and loop fasteners, touch fasteners), cam locks, interlocking mechanical couplings and/or other fasteners and/or engaging elements, and/or variants thereof and/or combinations thereof, in part or in their entirety. In some embodiments, an anchoring device can include a mating feature that engages and mates with a corresponding mating feature on a connecting structure in order to improve the stability of the coupling between the anchoring device and connecting structures. A mating feature can include one or more of protrusions, grooves, ribs, flanges, recesses, cavities, apertures, texturing, patterning, interlocking elements, and the like. Optionally, the mating features can be shaped to constrain the connecting structure to a specified position and/or orientation relative to the anchoring device, e.g., in order to maintain the connecting structure at a desired configuration relative to the patient's jaws. This can be used to constrain the jaws to a specific position relative to each other, for example.

Figure 8:
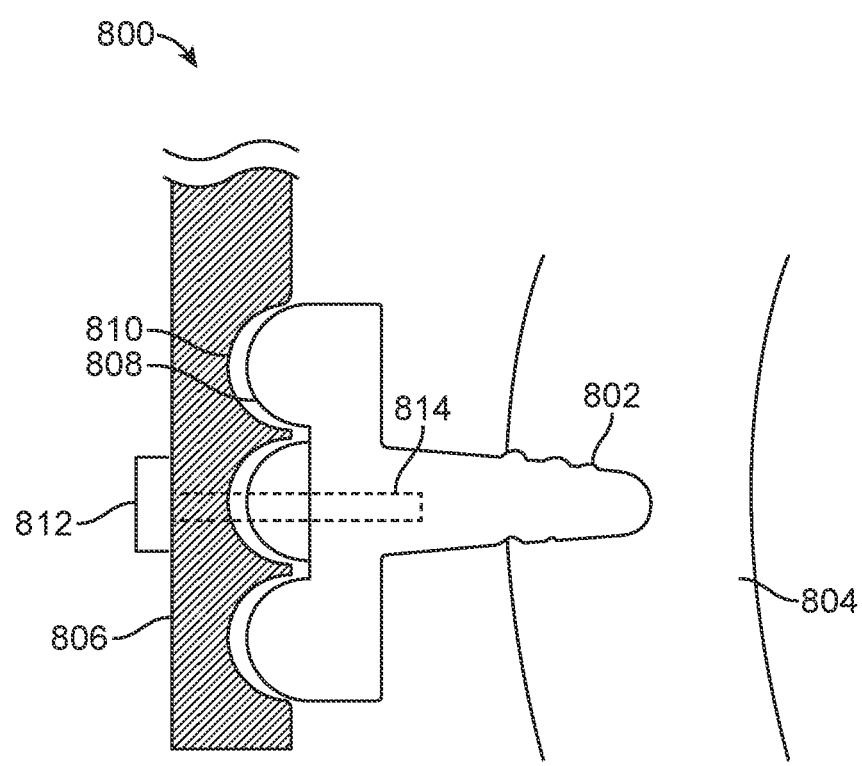
FIG. 8 illustrates a bone anchor with a mating feature for locating a rigid element which is part of an oral apparatus, in accordance with embodiments.

FIG. 8 illustrates part of an apparatus 800 comprising anchoring device 802 anchored into bone 804 and removably coupled to connecting structure 806 (e.g., a stiff connecting structure) by a mating feature that comprises locking surface 808 of the anchoring device 802 that removably engages and mates with locking surface 810 of the connecting structure 806. Anchoring device 802 is optionally also secured to connecting structure 806 by engaging element 812. The locking surface 808 can include, for example, one or more protrusions that are received within complementary recesses on the locking surface 810. However, it shall be appreciated that other types of complementary structures can be used to ensure a mating fit between the anchoring device 802 and connecting structure 806. In this embodiment, engaging element 812 comprises a removable fastener 814 that secures connecting structure 806 to anchoring device 802, but is hand-removable by the patient (e.g., can be removed without requiring tools), such as a thumbscrew. In other embodiments, the engaging element comprises other coupling means, including but not limited to snap-fit couplings, magnetic couplings, and/or other couplings of the present disclosure, which may or may not be patient-removable.

As described above and herein, the apparatus and devices of the present disclosure can constrain vertical movements of the lower jaw relative to the upper jaw while producing mandibular advancement and/or retraction. In some embodiments, the connecting structures and anchoring devices described herein can be arranged to limit the vertical movement range of the jaws (e.g., opening and closing jaw movements) while allowing free motion of the jaw within that range and, optionally, simultaneously positioning the mandible in the anterior and/or posterior direction (e.g. positioning it forward to open the airway for treatment of sleep apnea). For example, the range of motion in closing the jaw can be limited to prevent the possibility of bruxing, while the limit for opening the jaw could be set to allow the maximum natural opening or a smaller opening, as desired. This approach can improve patient comfort during mandibular advancement and/or retraction by permitting some jaw opening and closing movements, while reducing the incidence of unwanted side effects such as teeth clenching and bruxing.

Figure 13A:
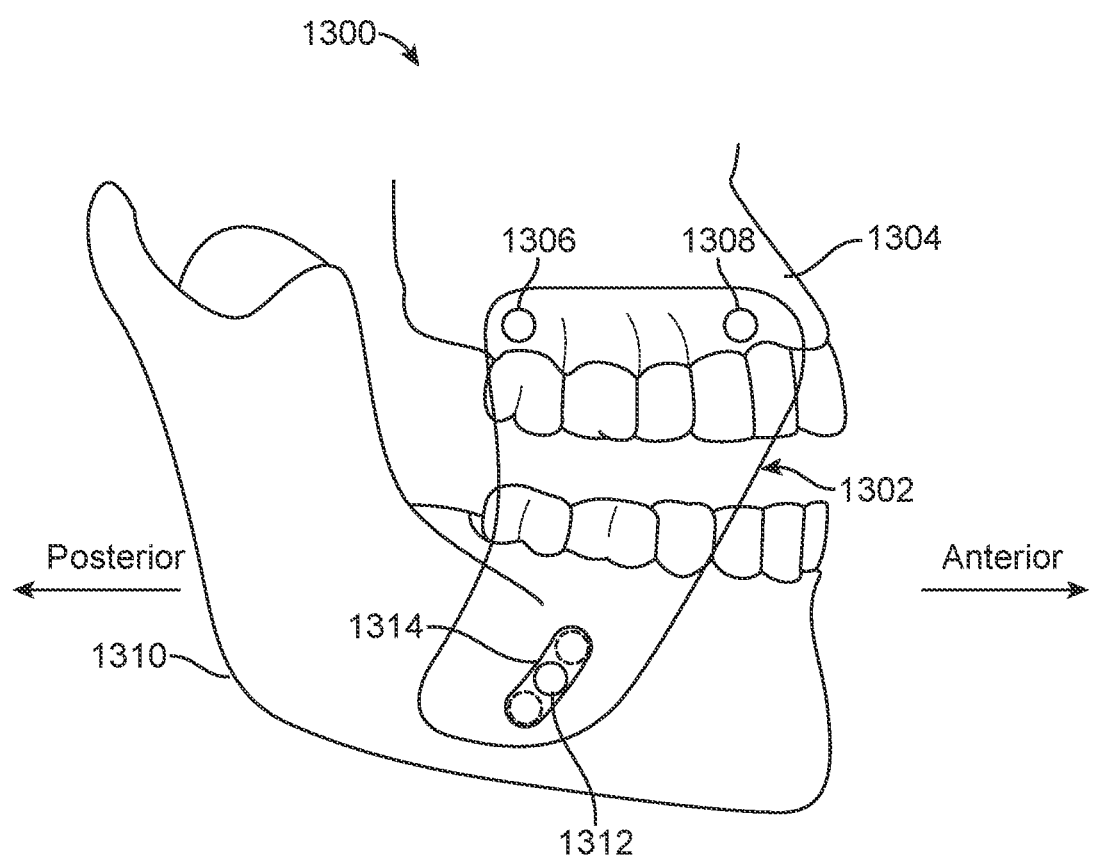
FIG. 13A illustrates an apparatus providing a limited range of vertical jaw movements when in position in a patient's intraoral cavity, in accordance with embodiments.
Figures 13B, 13C:
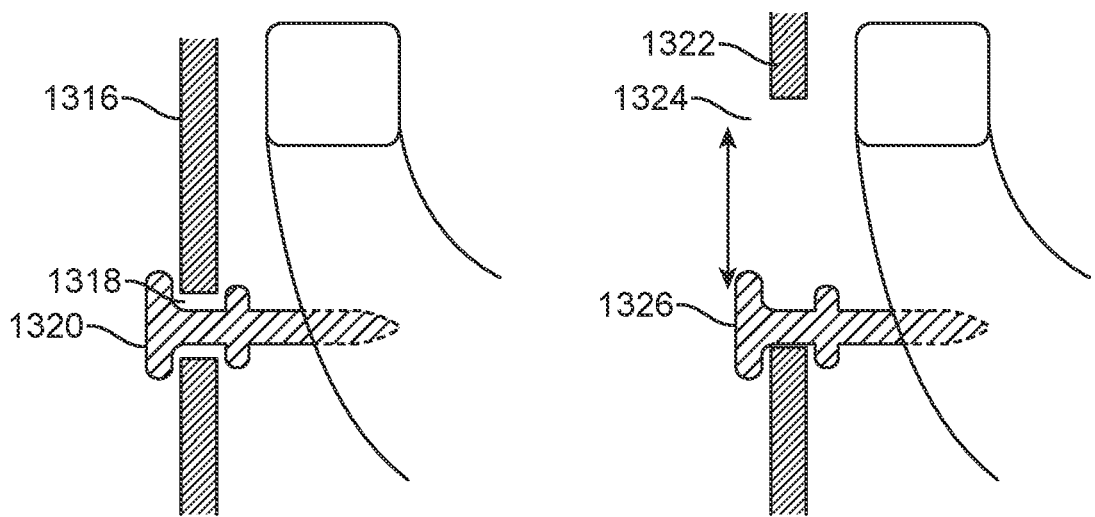
FIGS. 13B and 13C illustrate sectional views of connecting structures for controlling vertical jaw movements when in position in a patient's intraoral cavity, in accordance with embodiments.

FIG. 13A illustrates an apparatus 1300 providing a limited range of vertical jaw movements when in position in a patient's intraoral cavity, in accordance with embodiments. The apparatus 1300 includes a connecting structure 1302 coupled to upper jaw 1304 by anchoring devices 1306, 1308 and to lower jaw 1310 by anchoring device 1312. The anchoring device 1312 is received within a slot 1314 formed in the connecting structure 1302. The anchoring device 1312 can slide within the slot 1314 relative to the connecting structure 1302 so as to allow the lower jaw 1310 to be moved vertically relative to the upper jaw 1304 within a limited range. The range can be defined by the positioning and/or geometry of the slot 1314. For example, FIG. 13B illustrates a cross-sectional view of a connecting structure 1316 having a relatively short slot 1318 which provides little clearance for vertical motion of the anchoring device 1320, thus imposing a relatively severe constraint on the vertical movements of the jaws. In contrast, FIG. 13C illustrates a cross-sectional view of a connecting structure 1322 having a relatively long slot 1324 which provides greater freedom of vertical movement for the anchoring device 1326, and therefore permits an increased range of vertical motion for the jaws. Optionally, the slot 1314 can be curved so as to conform to the natural jaw opening and closing trajectory of the patient. Additionally, the positioning and/or geometry of the slot 1314 in the connecting structure 1302 can be used to control the amount of mandibular displacement produced by the apparatus 1300. For example, the position of the slot 1314 along the anterior-posterior direction relative to the natural position of the anchoring device 1312 (e.g., when the lower jaw 1310 is in a habitual or relaxed position) can determine the amount of mandibular displacement.

The mandibular advancement and/or retraction apparatus described herein can be used in conjunction with other intraoral appliances. The other appliance can be positioned on the upper jaw or the lower jaw. The other appliance can include a shell appliance (e.g., polymeric shell appliance), such as a tooth-repositioning appliance. The shell appliance can have teeth-receiving cavities shaped to receive and apply a resilient positioning force (e.g., tooth repositioning force) to the patient's teeth. In alternative embodiments, the teeth-receiving cavities can be shaped to maintain a current tooth arrangement, such that the shell appliance serves as a retainer for the teeth. Optionally, a shell appliance can reposition some teeth while maintaining other teeth in a current arrangement. In some embodiments, other types of tooth repositioning appliances can be used, such as wire-and-bracket appliances (e.g., braces).

As discussed herein, some embodiments of the systems, methods, devices and apparatus for mandibular advancement and/or retraction of the present disclosure produce displacements of the upper and/or lower jaws by applying forces directly to the bone of the jaws, with minimal or no forces applied to teeth or to periodontal ligaments. Accordingly, some embodiments of the systems, methods, devices and apparatus described herein can be used effectively in combination with tooth repositioning appliances because the mandibular displacement approaches described herein do not interfere with tooth repositioning forces applied by tooth repositioning appliances such as aligners. Advantageously, this allows for orthodontic treatments to be applied to the patient's teeth in conjunction with the mandibular advancement and/or retraction therapy.

In some embodiments, the apparatus presented herein can be combined with orthodontic treatment, particularly orthodontic treatment with removable aligners such as those available under the trade name Invisalign® from Align Technology, Inc. as described herein. If the patient has class II or class III malocclusions, for example, and movement of the teeth in the jaw is desired, the connecting structures can be attached to buttons or hooks on the upper or lower aligner to generate the desired forces. By using one or more anchoring devices, teeth on one jaw can be moved without moving teeth on the other.

Figure 9A:
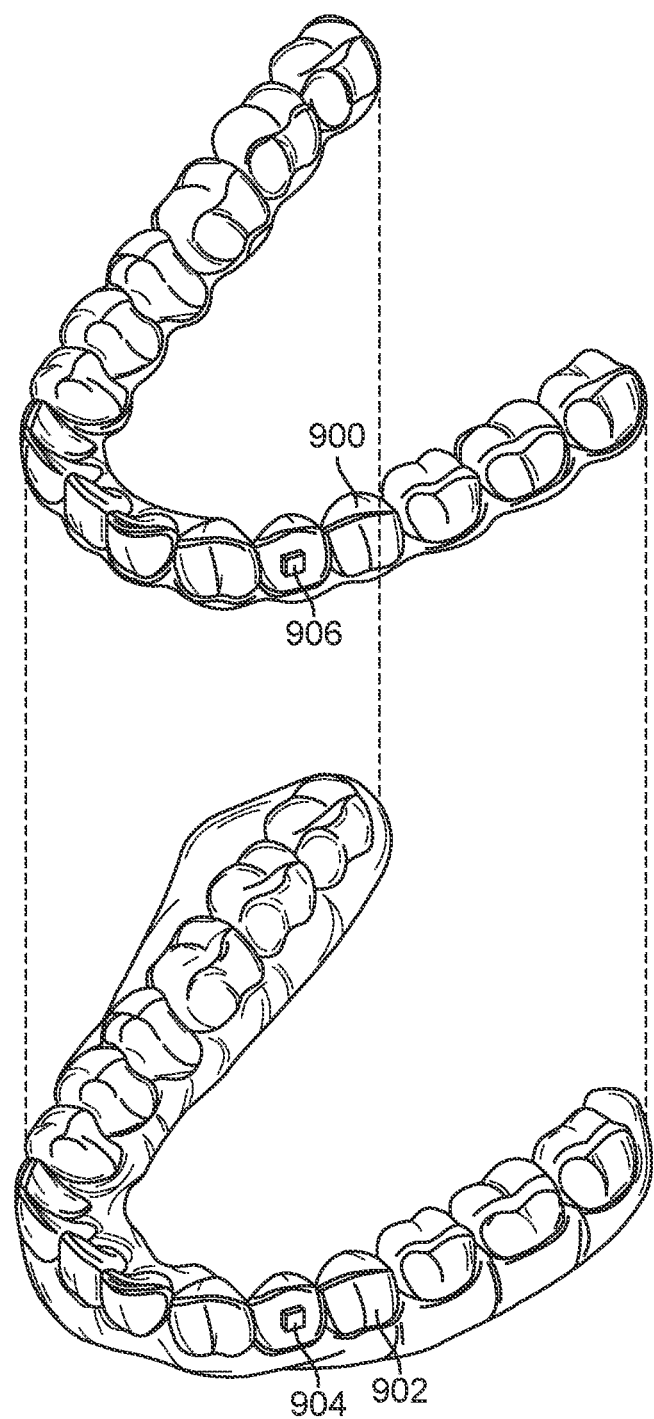
FIG. 9A illustrates a tooth repositioning appliance, in accordance with embodiments.

FIG. 9A illustrates an exemplary tooth repositioning appliance or aligner 900 suitable for incorporation with the embodiments described herein. The appliance 900 can be worn by a patient in order to achieve an incremental repositioning of individual teeth 902 in the jaw. The appliance can include a shell (e.g., a continuous polymeric shell or a segmented shell) having teeth-receiving cavities that receive and resiliently reposition the teeth. In one embodiment, an appliance or portion(s) thereof may be indirectly fabricated using a physical model of teeth. For example, an appliance (e.g., polymeric appliance) can be formed using a physical model of teeth and a sheet of suitable layers of polymeric material. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 904 on teeth 902 with corresponding receptacles or apertures 906 in the appliance 900 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 9B:
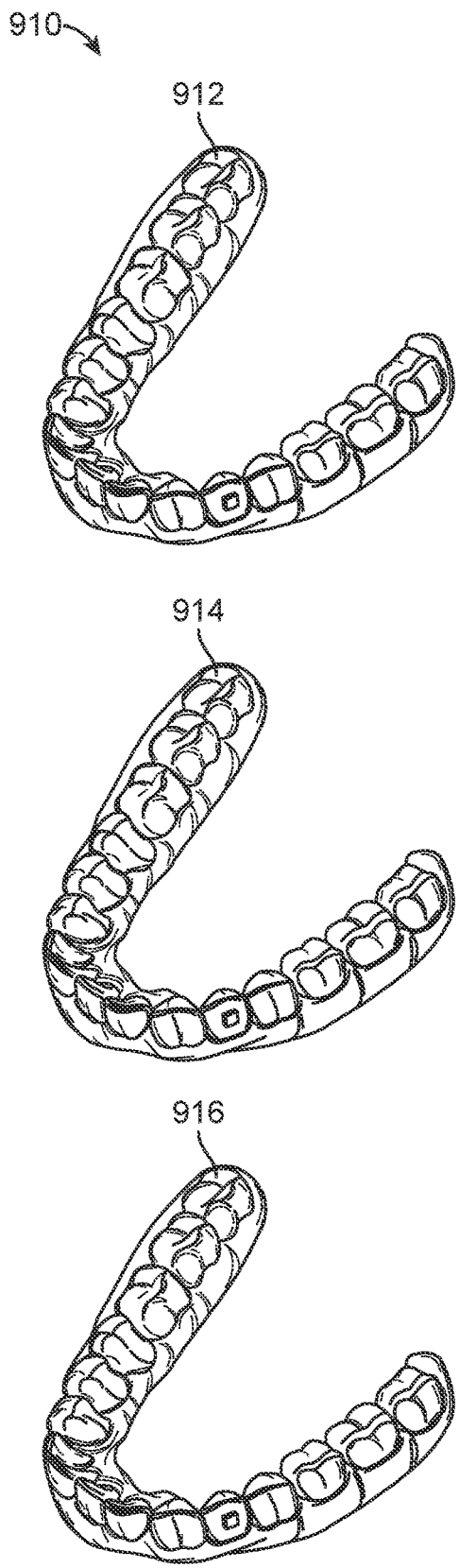
FIG. 9B illustrates a tooth repositioning system, in accordance with embodiments.

FIG. 9B illustrates a tooth repositioning system 910 including a plurality of appliances 912, 914, 916. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 910 can include a first appliance 912 corresponding to an initial tooth arrangement, one or more intermediate appliances 914 corresponding to one or more intermediate arrangements, and a final appliance 916 corresponding to a target arrangement. A target tooth arrangement can be a planned final tooth arrangement selected for the patient's teeth at the end of all planned orthodontic treatment. Alternatively, a target arrangement can be one of many intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implant, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 10:
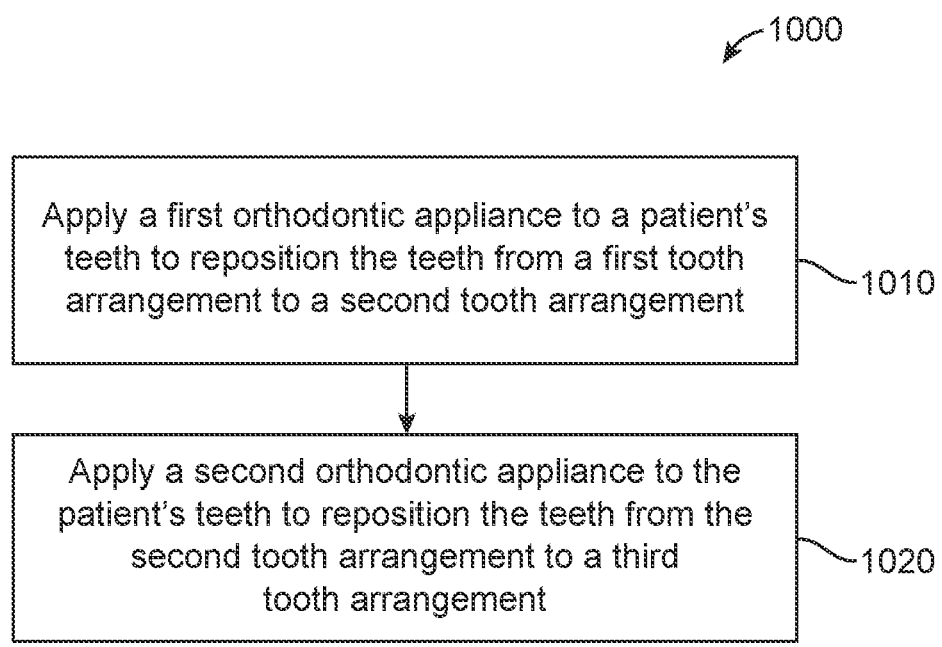
FIG. 10 illustrates a method of orthodontic treatment using a plurality of appliances, in accordance with use of embodiments.

FIG. 10 illustrates a method 1000 of orthodontic treatment using a plurality of appliances, in accordance with many embodiments. The method 1000 can be practiced using any of the appliances or appliance sets described herein. In step 1010, a first orthodontic appliance is applied to a patient's teeth in order to reposition the teeth from a first tooth arrangement to a second tooth arrangement. In step 1020, a second orthodontic appliance is applied to the patient's teeth in order to reposition the teeth from the second tooth arrangement to a third tooth arrangement. The method 1000 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

In some embodiments, a connecting structure of a mandibular advancement and/or retraction apparatus can be coupled to another appliance in the patient's intraoral cavity. For example, the connecting structure can include a first portion coupled to an anchoring device and a second portion coupled to the appliance. The appliance can be a shell appliance, such as an aligner or retainer. Optionally, the appliance can be a wire-and-bracket appliance. The coupling between the connecting structure and appliance can be removable, e.g., patient-removable, and can utilize any of the coupling mechanisms described herein. A connecting structure coupled to another appliance can be used to exert forces and/or moments on the patient's upper and/or lower jaws to displace the lower jaw. In some embodiments, a connecting structure coupled to an appliance can be used to exert tooth repositioning forces on teeth received by the appliance.

Alternatively or in combination, the connecting structures can include a connecting structure coupled to an anchoring device and coupled to an attachment positioned on at least one tooth of the upper jaw or the lower jaw. For example, the connecting structure can include a first portion coupled to an anchoring device and a second portion coupled to the attachment. Various attachments, including materials and designs, can be utilized. Attachments can include various materials, e.g., metal, glass, composite, plastic, etc. For example, attachments can be formed by application and in some cases curing of material (e.g., composite) on a tooth surface. Attachment materials can further include various pre-formed or pre-fabricated components, such as attachment devices. Materials for attachment positioning, such as templates, attachment materials, etc., can optionally be provided to an orthodontic practitioner for attachment positioning. Mounting an attachment can include bonding the attachment to the surface of the patient's tooth. Bonding and attachment positioning can be accomplished according to various techniques, including those commonly employed in orthodontics for mounting or bonding an attachment or object to a patient's tooth. The coupling between the connecting structure and attachment can be removable, e.g., patient-removable, and can utilize any of the coupling mechanisms described herein. A connecting structure coupled to an attachment can be used to exert forces and/or moments on the patient's upper and/or lower jaws to displace the lower jaw. Optionally, a connecting structure coupled to an attachment can be used to exert tooth repositioning forces on the tooth with the attachment.

Figure 11:
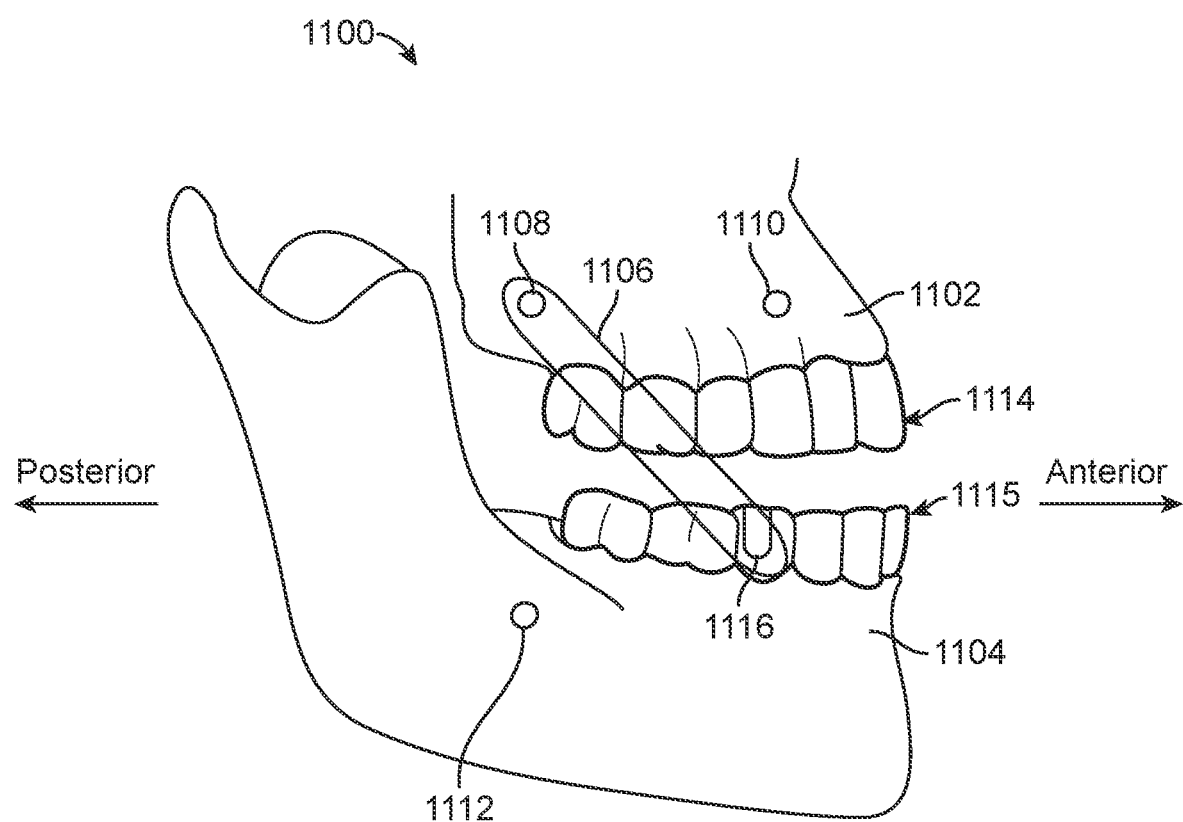
FIG. 11 illustrates an apparatus for mandibular advancement or retraction useable in combination with tooth repositioning aligners, in accordance with embodiments.

FIG. 11 illustrates an apparatus 1100 for mandibular advancement and/or retraction used in combination with tooth repositioning aligners, in accordance with embodiments. In some embodiments, the apparatus 1100 can be used with retainers or aligners which have attachment elements, such as (without limitation) hooks, buttons and/or wires and brackets. In FIG. 11, exemplary apparatus 1100 comprises upper tooth repositioning aligner 1114, lower tooth repositioning aligner 115, and connecting structure 1106 that is removably coupled to anchoring device 1108 positioned on upper jaw 1102. Connecting structure 1106 is also removably coupled to attachment element 1116 (e.g., hook, button, bracket) that is attached to lower tooth repositioning aligner 1115. In other embodiments, the attachment element 1116 can be attached to a tooth rather than to the aligner 1115, and the aligner 1115 can include a hole through which the attachment element 1116 extends. In this configuration, the apparatus generates a force system that displaces the lower jaw 1104 in a posterior direction relative to the upper jaw 1102, e.g., to treat malocclusion as part of a combined treatment, as discussed further herein. It shall be appreciated that in alternative embodiments the connecting structure 1106 can be removably coupled in a manner producing anterior displacement of the lower jaw 1104. Connecting structure 1106 can be removed from anchoring device 1108 and/or attachment element 1116, e.g., by the patient. In alternative embodiments, other configurations of the connecting structure 1106 can be used. Connecting structure 1106 can be coupled to anchoring device 1110 positioned on upper jaw 1102 and/or anchoring device 1112 positioned on lower jaw 1104. Apparatus 1100 is configured such that one or more connecting structures can be coupled to any combination of anchoring devices 1108, 1110 and 1112 and/or attachment element 1116 in order to achieve different desired displacements of lower jaw 1104 relative to upper jaw 1102 during different treatment phases.

In some embodiments, the anchoring devices can include a dental implant (e.g., a prosthesis such as a crown or bridge) positioned in the upper jaw or the lower jaw of the patient and the one or more connecting structures can include a connecting structure removably coupled to the dental implant. Because the dental implant, unlike a natural tooth, is not coupled to a periodontal ligament, application of force to the dental implant by a connecting structure is not expected to cause repositioning or displacement of the implant. By using preexisting anchoring devices already in the patient's intraoral cavity such as a dental implant, this approach can advantageously reduce the number of new anchoring devices that need to be placed.

The methods and apparatus provided herein can include applying more than one force system during more than one treatment phase to achieve different planned and/or desired displacements of the lower jaw relative to the upper jaw. The different displacements can be, for instance, different amounts of displacement, different directions of displacement, or combinations thereof. Different force systems can be used to produce the different displacements. For example, in some embodiments, a first force system is applied during a first treatment phase to displace the lower jaw anteriorly relative to the upper jaw, and a second force system is applied during a second treatment phase to displace the lower jaw posteriorly relative to the upper jaw. The different force systems can be achieved by using different arrangements and/or combinations of connecting structures coupled to anchoring devices as described herein. In some embodiments, a first one or more connecting structures are removably coupled to a first subset of a plurality of anchoring devices during the first treatment phase so as to apply the first force system to the upper and lower jaws, and a second one or more connecting structures are removably coupled to a second subset of the plurality of anchoring devices during the second treatment phase so as to apply the second force system to the upper and lower jaws.

The different force systems can be applied using the same or different connecting structures removably coupled to the same or different anchoring devices. For example, the first and second subsets of anchoring devices can be the same or different, and the first and second one or more connecting structures can be the same or different. Different force systems can be applied, e.g., via the same connecting structures removably coupled to different anchoring devices at different treatment phases, and/or via different connecting structures removably coupled to the same anchoring devices at different treatment phases, and/or via different connecting structures removably coupled to different anchoring devices at different treatment phases.

In some embodiments, the methods and apparatus provide for treating a patient via both mandibular advancement and mandibular retraction. Mandibular advancement (displacing the lower jaw anteriorly relative to the upper jaw) can be achieved by a first force system during a first treatment phase performed when the patient is asleep to minimize or eliminate obstruction of the airway to prevent or minimize the risk of sleep apnea and/or snoring. Mandibular retraction (displacing the lower jaw posteriorly relative to the upper jaw) can be achieved by a second force system during a second treatment phase performed when the patient is awake, and can serve, e.g., to correct a malocclusion, such as a class III malocclusion or any other malocclusion. For class III patients, the orthodontic movement can be opposite to that desired for treating sleep apnea. In this case, the connecting structures can be arranged to treat sleep apnea at night and the class III condition during the day, e.g., by swapping which anchoring devices are used with the connecting structures (e.g., elastic or stiff connecting structures).

Similarly, the tendency of existing sleep apnea treatments to procline the anterior teeth could be prevented by using different aligner features for day vs. night, optionally including different anchoring arrangements.

Figure 12A:
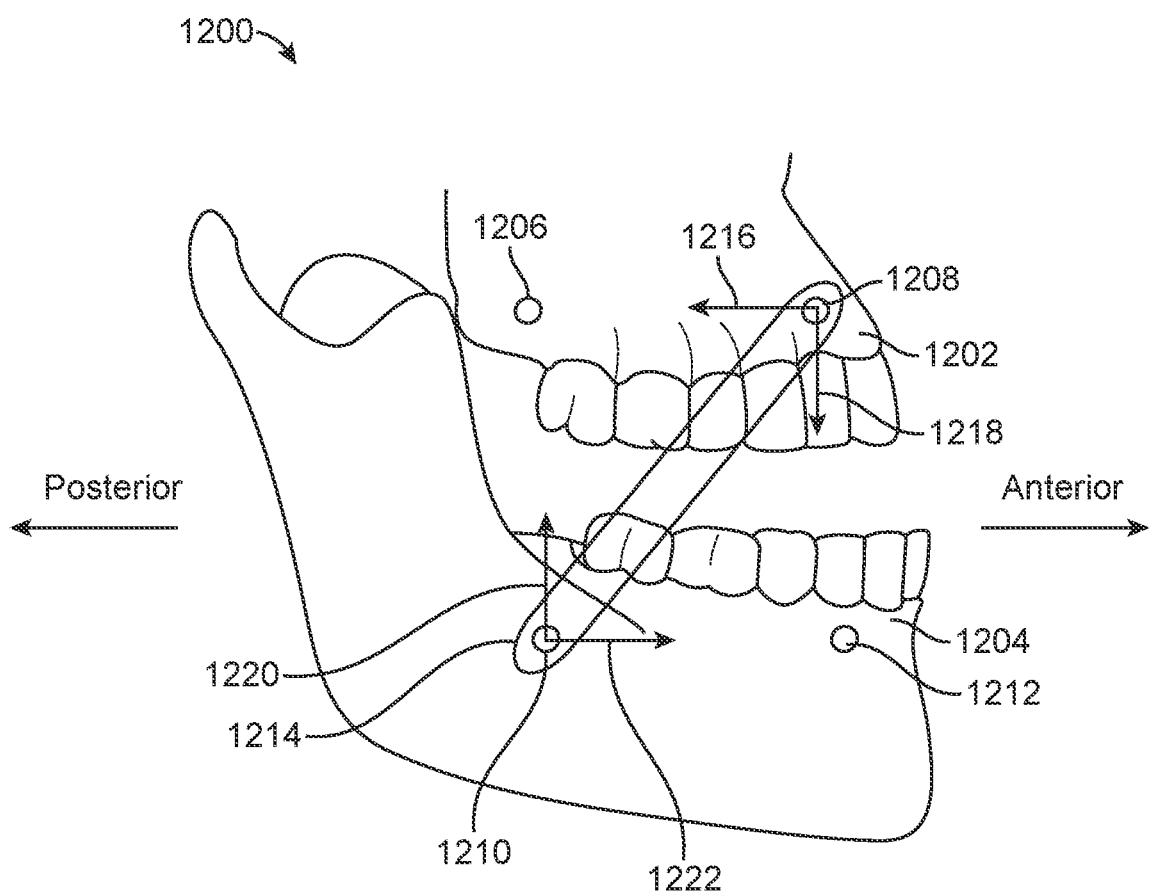
FIGS. 12A and 12B illustrate alternate positions for the treatment of apnea during sleep and the treatment of class I or class III occlusions during waking hours, in accordance with use of embodiments.
Figure 12B:
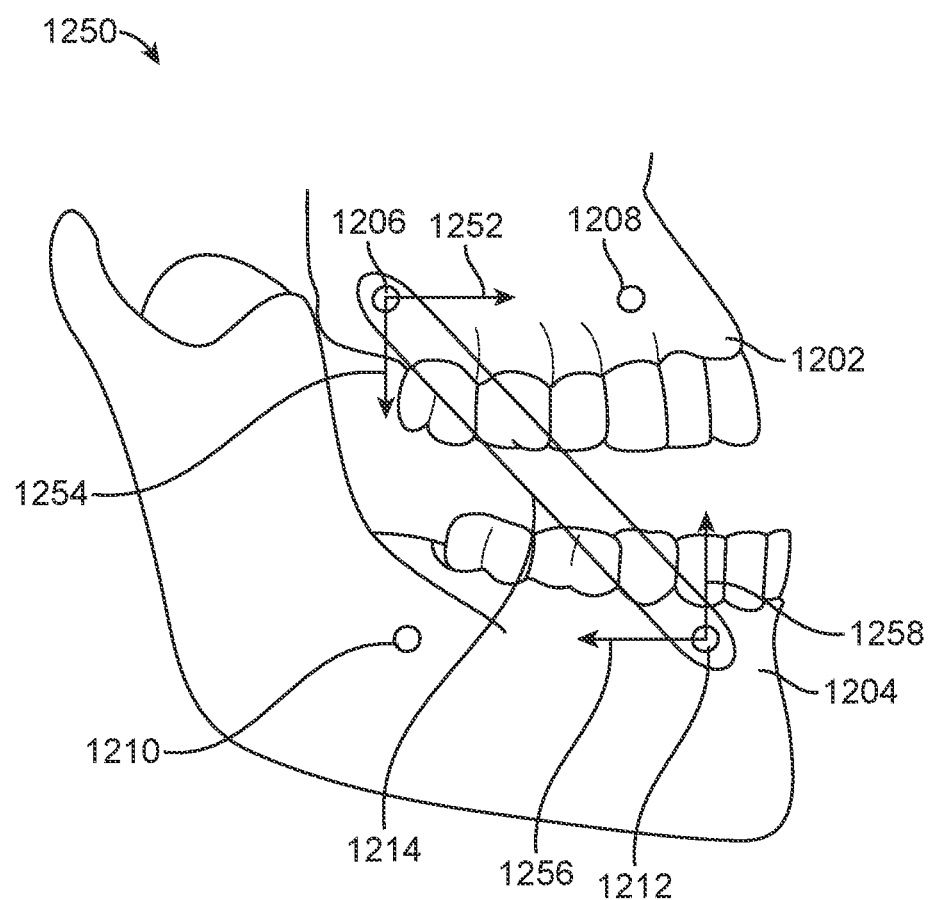

Systems, devices, methods and apparatus of the present disclosure comprise apparatus that can be configured to achieve different jaw displacements during different phases of treatments. For example, in some embodiments, an apparatus is configured to achieve an anterior displacement of the lower jaw relative to the upper jaw for treatment of sleep apnea during a night/sleeping treatment phase and to achieve a posterior displacement of the lower jaw relative to the upper jaw for treatment of class I and/or class III malocclusions during a day/waking treatment phases. FIGS. 12A and 12B show how an exemplary oral apparatus can be reversibly configured to selectively treat apnea and/or class I or III malocclusions during distinct treatment phases. The apparatus can include a connecting structure that can be installed over bone anchoring devices positioned to advance the lower jaw to treat apnea, as shown in FIG. 12A, or over other bone anchoring devices positioned to retract the lower jaw to treat orthodontic occlusions as shown in FIG. 12B. Alternating mandibular advancement and retraction as depicted in FIGS. 12A and 12B can be beneficial, for example, when treating growing patients for sleep apnea without producing changes in the temporomandibular joint (TMJ) that could produce class III malocclusion. Optionally, the apparatus can be used in combination with another orthodontic appliance, such as the tooth repositioning aligners described herein. In such embodiments, at least one portion of the connecting structure can be coupled to the appliance, e.g., as described herein with respect to FIG. 11.

FIG. 12A depicts apparatus configuration 1200, for displacing the lower jaw anteriorly relative to the upper jaw during a first treatment phase. In use, elastic connecting structure 1214 is removably coupled to anchoring device 1208 positioned on upper jaw 1202, and is removably coupled to anchoring device 1210 positioned on lower jaw 1204. Anchoring device 1208 is positioned anteriorly relative to anchoring device 1210 such that a tension in elastic connecting structure 1214 applies an anterior force 1222 to cause anterior displacement (advancement) of lower jaw 1204. Similarly, an equal and opposite posterior force 1216 is applied to upper jaw 1202 by elastic connecting structure 1214. Tension in elastic connecting structure 1214 also applies downward vertical force 1218 that can cause downward vertical displacement of upper jaw 1202, and upward vertical force 1220 that can cause upward vertical displacement of lower jaw 1204. In other embodiments of the present disclosure, these vertical displacements are restricted, e.g., by the use of one or more stiff connecting structures, application of one or more moments, or combinations thereof.

FIG. 12B depicts apparatus configuration 1250, for displacing the lower jaw posteriorly relative to the upper jaw during a second treatment phase. Elastic connecting structure 1214 is removably coupled to anchoring device 1206 positioned on upper jaw 1202, and is removably coupled to anchoring device 1212 positioned on lower jaw 1204. Anchoring device 1206 is positioned posteriorly relative to anchoring device 1212 such that a tension in elastic connecting structure 1214 applies a posterior force 1256 to cause posterior displacement (retraction) of lower jaw 1204. Similarly, an equal and opposite anterior force 1252 is applied to upper jaw 1202 by elastic connecting structure 1214. Tension in elastic connecting structure 1214 also applies downward vertical force 1254 that can cause downward vertical displacement of upper jaw 1202, and upward vertical force 1258 that can cause upward vertical displacement of lower jaw 1204. In other embodiments of the present disclosure, these vertical displacements are restricted, e.g. by the use of one or more stiff connecting structures, application of one or more moments, or combinations thereof.

Systems, devices, methods and apparatus of the present disclosure comprise embodiments that can be digitally designed. In some embodiments, apparatus of the present disclosure are designed and/or fabricated based on digital representations of the patient's teeth and jaws. Computer-based approaches such as computer modeling techniques can be used to determine and/or predict forces and/or moments that will be applied to teeth and/or jaws by apparatus described herein, and/or components thereof (e.g., connecting structures and/or anchoring devices). Computer-based approaches such as computer modeling techniques can also be used to determine and/or predict forces and/or moments that will be applied to the apparatus described herein, and/or components thereof, by teeth and/or jaws.

The geometry and arrangement of the connecting structures and/or anchoring devices described herein can also be digitally designed. In some aspects, one or more representations of the patient's teeth and/or jaws are provided, along with a desired or planned displacement of the lower jaw relative to the upper jaw, as inputs to one or more computer-based models. The one or more computer-based models can determine, based on these inputs, the geometry and/or arrangement of the apparatus and/or components thereof, and/or materials or physical properties (e.g. elastic modulus) of the components thereof, so as to apply a force system suitable to achieve one or more desired displacements of the lower jaw relative to the upper jaw in accordance with one or more treatment phases.

The various techniques described herein may be partially or fully implemented using code that is storable upon storage media and computer readable media, and executable by one or more processors of a computer system. The processor can comprise array logic such as programmable array logic (hereinafter PAL), configured to perform the techniques described herein. Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:

1. An apparatus for treating a patient via mandibular advancement or retraction, the apparatus comprising:
    a plurality of anchoring devices configured to be positioned in bone of the patient's upper jaw or bone of the patient's lower jaw; and
    one or more connecting structures removably couplable to and configured to extend between the plurality of anchoring devices to produce an anterior-posterior force component greater than a vertical force component along a vertical direction to displace the lower jaw anteriorly or posteriorly relative to the upper jaw.

2. The apparatus of claim 1, wherein the vertical force component is zero.

3. The apparatus of claim 1, wherein the one or more connecting structures are removably couplable to the plurality of anchoring devices by a mechanism.

4. The apparatus of claim 3, wherein the mechanism is selected from one of a snap-fit coupling, magnetic coupling, interference fit, locking surface, adhesive, removable fastener, cam lock, interlocking mechanical coupling, or fastening feature.

5. The apparatus of claim 1, wherein the one or more connecting structures comprise an elastic structure.

6. The apparatus of claim 5, wherein the elastic structure is configured to exert anterior-posterior forces without applying vertical forces.

7. The apparatus of claim 1, wherein the one or more connecting structures comprise a stiff structure.

8. The apparatus of claim 7, wherein the stiff structure exhibits substantially no deformation under load.

9. The apparatus of claim 1, wherein the connecting structure comprises a plate structure.

10. The apparatus of claim 9, wherein the plate structure comprises a geometry selected from one of a circular, elliptical, triangular, and rectangular geometry.

11. A method for treating a patient via mandibular advancement or retraction, the method comprising:
    positioning a plurality of anchoring devices in bone of the patient's upper jaw or bone of the patient's lower jaw; and
    removably coupling one or more connecting structures to the plurality of anchoring devices, wherein the one or more connecting structures extends between the plurality of anchoring devices in order to produce an anterior-posterior force component greater than a vertical force component along a vertical direction to displace the lower jaw in an anterior-posterior direction relative to the upper jaw.

12. The method of claim 11, wherein the vertical force component is zero.

13. The method of claim 11, wherein the one or more connecting structures are removably couplable to the plurality of anchoring devices by a mechanism.

14. The method of claim 13, wherein the mechanism is selected from one of a snap-fit coupling, magnetic coupling, interference fit, locking surface, adhesive, removable fastener, cam lock, interlocking mechanical coupling, or fastening feature.

15. The method of claim 11, wherein the one or more connecting structures comprise an elastic structure.

16. The method of claim 15, wherein the elastic structure is configured to exert anterior-posterior forces without applying vertical forces.

17. The method of claim 11, wherein the one or more connecting structures comprise a stiff structure.

18. The method of claim 17, wherein the stiff structure exhibits substantially no deformation under load.

19. The method of claim 11, wherein the connecting structure comprises a plate structure.

20. The method of claim 19, wherein the plate structure comprises a geometry selected from one of a circular, elliptical, triangular, and rectangular geometry.

* * * * *